US009791445B2

(12) United States Patent
Richt et al.

(10) Patent No.: US 9,791,445 B2
(45) Date of Patent: Oct. 17, 2017

(54) RIFT VALLEY FEVER VIRUS GLYCOPROTEINS, GN AND GC, AND THEIR USE

(71) Applicant: Kansas State University Research Foundation, Manhattan, KS (US)

(72) Inventors: Juergen A. Richt, Manhattan, KS (US); Bonto Faburay, Manhattan, KS (US); William Wilson, Westmoreland, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 14/166,841

(22) Filed: Jan. 28, 2014

(65) Prior Publication Data

US 2014/0212447 A1    Jul. 31, 2014

Related U.S. Application Data

(60) Provisional application No. 61/757,538, filed on Jan. 28, 2013, provisional application No. 61/916,784, filed on Dec. 16, 2013.

(51) Int. Cl.
| | |
|---|---|
| *A61K 39/12* | (2006.01) |
| *C07K 14/005* | (2006.01) |
| *G01N 33/569* | (2006.01) |
| *C07K 16/10* | (2006.01) |

(52) U.S. Cl.
CPC ....... *G01N 33/56983* (2013.01); *A61K 39/12* (2013.01); *C07K 14/005* (2013.01); *C07K 16/10* (2013.01); *C12N 2760/12222* (2013.01); *C12N 2760/12234* (2013.01)

(58) Field of Classification Search
CPC ...... A61K 39/12; A61K 38/00; A61K 38/162; C07K 14/175; C12N 2760/12211; C12N 2510/02
See application file for complete search history.

(56) References Cited

U.S. PATENT DOCUMENTS

| | | | | |
|---|---|---|---|---|
| 8,673,629 | B2 * | 3/2014 | Bird | A61K 39/12 424/93.2 |
| 9,045,727 | B2 * | 6/2015 | Compans | A61K 39/12 |
| 2006/0088909 | A1 * | 4/2006 | Compans | C07K 14/005 435/69.1 |
| 2009/0123494 | A1 * | 5/2009 | Staplin | A61K 39/12 424/205.1 |
| 2011/0110976 | A1 * | 5/2011 | Weber | A61K 39/12 424/204.1 |

\* cited by examiner

*Primary Examiner* — Bao Li

(57) ABSTRACT

The present invention describes subunit vaccines containing Gn and Gc glycoproteins of the Rift Valley Fever Virus, including nucleic acids encoding such glycoproteins, host cells, vectors, and immunoreagents generated with the glycoproteins, methods of vaccination, methods of diagnosis, and kits.

3 Claims, 11 Drawing Sheets

FIG. 6

SEQUENCE LISTING

```
<160> NUMBER OF SEQ ID NOS: 21

<210> SEQ ID NO 1
<211> LENGTH: 54
<212> TYPE: DNA
<213> ORGANISM: Rift Valley fever virus
<220> FEATURE:
<221> NAME/KEY: sig_peptide
<222> LOCATION: (1)..(54)

<400> SEQUENCE: 1
atgacagtcc ttccagcctt agcagttttt gctttggcac ctgttgtttt tgct            54

<210> SEQ ID NO 2
<211> LENGTH: 18
<212> TYPE: PRT
<213> ORGANISM: Rift Valley fever virus
<220> FEATURE:
<221> NAME/KEY: signal
<222> LOCATION: (1)..(18)

<400> SEQUENCE: 2

Met Thr Val Leu Pro Ala Leu Ala Val Phe Ala Leu Ala Pro Val Val
1               5                   10                  15

Phe Ala

<210> SEQ ID NO 3
<211> LENGTH: 1354
<212> TYPE: DNA
<213> ORGANISM: Rift Valley fever virus
<220> FEATURE:
<221> NAME/KEY: Kozak
<222> LOCATION: (1)..(4)
<220> FEATURE:
<221> NAME/KEY: sig_peptide
<222> LOCATION: (5)..(58)

<400> SEQUENCE: 3
caccatgaca gtccttccag ccttagcagt ttttgctttg gcacctgttg tttttgctga     60
```

-continued

```
agaccccat ctcagaaaca gaccagggaa ggggcacaac tacattgacg ggatgactca    120
ggaggatgcc acatgcaaac ctgtgacata tgctggggca tgtagcagtt ttgatgtctt    180
gcttgaaaag ggaaaatttc ccctttcca gtcgtatgct catcatagaa ctctactaga    240
ggcagttcac gacaccatca ttgcaaaggc tgatccacct agctgtgacc ttctgagtgc    300
tcatgggaac ccctgcatga agagaaact cgtgatgaag acacactgtc caaatgacta    360
ccagtcagct cattacctca caatgacgg gaaaatggct tcagtcaagt gccctcctaa    420
gtatgagctc actgaggact gcaacttttg taggcagatg acaggtgcta gcctgaagaa    480
ggggtcttat cctctccaag acttgttttg tcagtcaagt gaggatgatg gatcaaaatt    540
aaaaacaaaa atgaaagggg tctgcgaagt gggggttcaa gcactcaaaa agtgtgatgg    600
ccaactcagc actgcacatg aggttgtgcc ctttgcagtg tttaagaact caaagaaggt    660
ttatcttgat aagcttgacc ttaagactga ggagaatctg ctaccagact catttgtctg    720
tttcgagcat aagggacagt acaaaggaac aatggactct ggtcagacta agagggagct    780
caaaagcttt gatatctctc agtgccccaa gattggagga catggtagta agaagtgcac    840
tggggacgca gcattttgct ctgcttatga gtgcactgct cagtacgcca atgcctattg    900
ttcacatgct aatgggtcag ggattgtgca gatacaagta tcagggggtct ggaagaagcc    960
tttatgtgta gggtatgaga gagtggttgt gaagagagaa ctctctgcca agcccatcca    1020
gagagttgag ccttgcacaa cttgtataac caaatgtgag cctcatggat tggttgtccg    1080
atcaacaggg ttcaagatat catcagcagt tgcttgtgct agcggagttt gcgtcacagg    1140
atcgcagagt ccttccaccg agattacact caagtatcca gggatatccc agtcttctgg    1200
gggggacata ggggttcaca tggcacacga tgatcagtca gttagctcca aaatagtagc    1260
tcactgccct ccccaggacc cgtgcttagt gcatgactgc atagtgtgtg ctcatggcct    1320
gataaaattac cagtgtcaca ctgctctcag tgcc                               1354
```

<210> SEQ ID NO 4
<211> LENGTH: 450
<212> TYPE: PRT
<213> ORGANISM: Rift Valley fever virus
<220> FEATURE:
<221> NAME/KEY: SIGNAL
<222> LOCATION: (1)..(18)

<400> SEQUENCE: 4

```
Met Thr Val Leu Pro Ala Leu Ala Val Phe Ala Leu Ala Pro Val Val
1               5                   10                  15

Phe Ala Glu Asp Pro His Leu Arg Asn Arg Pro Gly Lys Gly His Asn
                20                  25                  30

Tyr Ile Asp Gly Met Thr Gln Glu Asp Ala Thr Cys Lys Pro Val Thr
            35                  40                  45

Tyr Ala Gly Ala Cys Ser Ser Phe Asp Val Leu Leu Glu Lys Gly Lys
        50                  55                  60

Phe Pro Leu Phe Gln Ser Tyr Ala His His Arg Thr Leu Leu Glu Ala
65                  70                  75                  80

Val His Asp Thr Ile Ile Ala Lys Ala Asp Pro Pro Ser Cys Asp Leu
                85                  90                  95

Leu Ser Ala His Gly Asn Pro Cys Met Lys Glu Lys Leu Val Met Lys
                100                 105                 110

Thr His Cys Pro Asn Asp Tyr Gln Ser Ala His Tyr Leu Asn Asn Asp
            115                 120                 125
```

Gly Lys Met Ala Ser Val Lys Cys Pro Pro Lys Tyr Glu Leu Thr Glu
130                 135                 140

Asp Cys Asn Phe Cys Arg Gln Met Thr Gly Ala Ser Leu Lys Lys Gly
145                 150                 155                 160

Ser Tyr Pro Leu Gln Asp Leu Phe Cys Gln Ser Ser Glu Asp Asp Gly
                165                 170                 175

Ser Lys Leu Lys Thr Lys Met Lys Gly Val Cys Glu Val Gly Val Gln
            180                 185                 190

Ala Leu Lys Lys Cys Asp Gly Gln Leu Ser Thr Ala His Glu Val Val
        195                 200                 205

Pro Phe Ala Val Phe Lys Asn Ser Lys Lys Val Tyr Leu Asp Lys Leu
210                 215                 220

Asp Leu Lys Thr Glu Glu Asn Leu Leu Pro Asp Ser Phe Val Cys Phe
225                 230                 235                 240

Glu His Lys Gly Gln Tyr Lys Gly Thr Met Asp Ser Gly Gln Thr Lys
                245                 250                 255

Arg Glu Leu Lys Ser Phe Asp Ile Ser Gln Cys Pro Lys Ile Gly Gly
            260                 265                 270

His Gly Ser Lys Lys Cys Thr Gly Asp Ala Ala Phe Cys Ser Ala Tyr
        275                 280                 285

Glu Cys Thr Ala Gln Tyr Ala Asn Ala Tyr Cys Ser His Ala Asn Gly
290                 295                 300

Ser Gly Ile Val Gln Ile Gln Val Ser Gly Val Trp Lys Lys Pro Leu
305                 310                 315                 320

Cys Val Gly Tyr Glu Arg Val Val Val Lys Arg Glu Leu Ser Ala Lys
                325                 330                 335

Pro Ile Gln Arg Val Glu Pro Cys Thr Thr Cys Ile Thr Lys Cys Glu
            340                 345                 350

Pro His Gly Leu Val Val Arg Ser Thr Gly Phe Lys Ile Ser Ser Ala
        355                 360                 365

Val Ala Cys Ala Ser Gly Val Cys Val Thr Gly Ser Gln Ser Pro Ser
370                 375                 380

Thr Glu Ile Thr Leu Lys Tyr Pro Gly Ile Ser Gln Ser Ser Gly Gly
385                 390                 395                 400

Asp Ile Gly Val His Met Ala His Asp Asp Gln Ser Val Ser Ser Lys
                405                 410                 415

Ile Val Ala His Cys Pro Pro Gln Asp Pro Cys Leu Val His Asp Cys
            420                 425                 430

Ile Val Cys Ala His Gly Leu Ile Asn Tyr Gln Cys His Thr Ala Leu
        435                 440                 445

Ser Ala
450

<210> SEQ ID NO 5
<211> LENGTH: 1579
<212> TYPE: DNA
<213> ORGANISM: Rift Valley fever virus
<220> FEATURE:
<221> NAME/KEY: Kozak
<222> LOCATION: (1)..(4)
<220> FEATURE:
<221> NAME/KEY: sig_peptide
<222> LOCATION: (5)..(58)

<400> SEQUENCE: 5
caccatgaca gtccttccag ccttagcagt ttttgctttg gcacctgttg tttttgcttg     60

```
ttcagaactg attcaggcaa gctccagaat caccacttgc tctacagagg gtgttaacac    120
caagtgtaga ctgtctggca cagcattgat cagagcaggg tcagttgggg cagaggcttg    180
tttgatgttg aaggggggtca aggaagatca aaccaagttc ttaaagataa aaactgtctc    240
aagtgagcta tcatgcaggg agggccagag ttattggact gggtccttta gccctaaatg    300
tttgagctca aggagatgcc accttgtcgg ggaatgccat gtgataggt gtctgtcttg     360
gagggacaat gaaacttcag cagagttttc atttgttggg gaaagcacga ccatgcgaga    420
gaataagtgt tttgagcaat gtggaggatg ggggtgtggg tgtttcaatg tgaacccatc    480
ttgcttattt gtgcacacgt atctgcagtc agttagaaaa gaggccctta gagttttaa     540
ctgtatcgac tgggtgcata aactcactct agagatcaca gactttgatg ctctgtttc     600
aacaatagac ttgggagcat catctagccg tttcacaaac tggggttcag ttagcctctc    660
actggacgca gagggcattt caggctcaaa tagcttttct ttcattgaga gcccaggcaa    720
agggtatgca attgttgatg agccattctc agaaattcct cggcaagggt tcttggggga    780
gatcaggtgc aattcagagt cctcagtcct gagtgctcat gaatcatgcc ttagggcacc    840
aaaccttatc tcatacaagc ccatgataga tcaattggag tgcacaacaa atctgattga    900
tcccttttgtt gtctttgaga ggggttctct gccacagaca aggaatgaca aaaccttgc    960
agcttcaaaa ggaaatagag gtgttcaagc tttctctaag gctctgtac aagctgatct    1020
aactctgatg tttgacaatt ttgaggtgga cttttgtggga gcagccgtat cttgtgatgc    1080
cgccttctta aatttgacag gttgctattc ttgcaatgca ggggccaggg tctgcctgtc    1140
tatcacatcc acaggaactg gatctctctc tgcccacaat aaggatgggt ctctgcatat    1200
agtccttcca tcagagaatg gaacaaaaga ccagtgtcag atactacact tcactgtgcc    1260
tgaagtagag gaggagttta tgtactcttg tgatggagat gagcggcctc tgttggtgaa    1320
ggggacccctg atagccattg atccatttga tgataggcgg gaagcagggg gggaatcaac    1380
agttgtgaat ccaaaatctg gatcttggaa tttctttgac tggttttctg gactcatgag    1440
ttggtttgga gggcctctta aaactatact cctcatttgc ctgtatgttg cattatcaat    1500
tgggctcttt tcctccttta tatatctgg aagaacaggc ctctctaaaa gtgtggcttgc    1560
tgccactaag aaggcctca                                                1579
```

<210> SEQ ID NO 6
<211> LENGTH: 525
<212> TYPE: PRT
<213> ORGANISM: Rift Valley fever virus
<220> FEATURE:
<221> NAME/KEY: SIGNAL
<222> LOCATION: (1)..(18)

<400> SEQUENCE: 6

```
Met Thr Val Leu Pro Ala Leu Ala Val Phe Ala Leu Ala Pro Val Val
1               5                  10                  15

Phe Ala Cys Ser Glu Leu Ile Gln Ala Ser Ser Arg Ile Thr Thr Cys
            20                  25                  30

Ser Thr Glu Gly Val Asn Thr Lys Cys Arg Leu Ser Gly Thr Ala Leu
        35                  40                  45

Ile Arg Ala Gly Ser Val Gly Ala Glu Ala Cys Leu Met Leu Lys Gly
    50                  55                  60

Val Lys Glu Asp Gln Thr Lys Phe Leu Lys Ile Lys Thr Val Ser Ser
65                  70                  75                  80

Glu Leu Ser Cys Arg Glu Gly Gln Ser Tyr Trp Thr Gly Ser Phe Ser
```

```
                       85                  90                  95
Pro Lys Cys Leu Ser Ser Arg Arg Cys His Leu Val Gly Glu Cys His
            100                 105                 110

Val Asn Arg Cys Leu Ser Trp Arg Asp Asn Glu Thr Ser Ala Glu Phe
            115                 120                 125

Ser Phe Val Gly Glu Ser Thr Thr Met Arg Glu Asn Lys Cys Phe Glu
130                 135                 140

Gln Cys Gly Gly Trp Gly Cys Gly Cys Phe Asn Val Asn Pro Ser Cys
145                 150                 155                 160

Leu Phe Val His Thr Tyr Leu Gln Ser Val Arg Lys Glu Ala Leu Arg
                165                 170                 175

Val Phe Asn Cys Ile Asp Trp Val His Lys Leu Thr Leu Glu Ile Thr
            180                 185                 190

Asp Phe Asp Gly Ser Val Ser Thr Ile Asp Leu Gly Ala Ser Ser Ser
            195                 200                 205

Arg Phe Thr Asn Trp Gly Ser Val Ser Leu Ser Leu Asp Ala Glu Gly
            210                 215                 220

Ile Ser Gly Ser Asn Ser Phe Ser Phe Ile Glu Ser Pro Gly Lys Gly
225                 230                 235                 240

Tyr Ala Ile Val Asp Glu Pro Phe Ser Glu Ile Pro Arg Gln Gly Phe
                245                 250                 255

Leu Gly Glu Ile Arg Cys Asn Ser Glu Ser Ser Val Leu Ser Ala His
            260                 265                 270

Glu Ser Cys Leu Arg Ala Pro Asn Leu Ile Ser Tyr Lys Pro Met Ile
            275                 280                 285

Asp Gln Leu Glu Cys Thr Thr Asn Leu Ile Asp Pro Phe Val Val Phe
            290                 295                 300

Glu Arg Gly Ser Leu Pro Gln Thr Arg Asn Asp Lys Thr Phe Ala Ala
305                 310                 315                 320

Ser Lys Gly Asn Arg Gly Val Gln Ala Phe Ser Lys Gly Ser Val Gln
                325                 330                 335

Ala Asp Leu Thr Leu Met Phe Asp Asn Phe Glu Val Asp Phe Val Gly
            340                 345                 350

Ala Ala Val Ser Cys Asp Ala Ala Phe Leu Asn Leu Thr Gly Cys Tyr
            355                 360                 365

Ser Cys Asn Ala Gly Ala Arg Val Cys Leu Ser Ile Thr Ser Thr Gly
            370                 375                 380

Thr Gly Ser Leu Ser Ala His Asn Lys Asp Gly Ser Leu His Ile Val
385                 390                 395                 400

Leu Pro Ser Glu Asn Gly Thr Lys Asp Gln Cys Gln Ile Leu His Phe
                405                 410                 415

Thr Val Pro Glu Val Glu Glu Phe Met Tyr Ser Cys Asp Gly Asp
            420                 425                 430

Glu Arg Pro Leu Leu Val Lys Gly Thr Leu Ile Ala Ile Asp Pro Phe
            435                 440                 445

Asp Asp Arg Arg Glu Ala Gly Gly Glu Ser Thr Val Val Asn Pro Lys
            450                 455                 460

Ser Gly Ser Trp Asn Phe Phe Asp Trp Phe Ser Gly Leu Met Ser Trp
465                 470                 475                 480

Phe Gly Gly Pro Leu Lys Thr Ile Leu Leu Ile Cys Leu Tyr Val Ala
                485                 490                 495

Leu Ser Ile Gly Leu Phe Phe Leu Leu Ile Tyr Leu Gly Arg Thr Gly
            500                 505                 510
```

Leu Ser Lys Met Trp Leu Ala Ala Thr Lys Lys Ala Ser
            515                 520                 525

<210> SEQ ID NO 7
<211> LENGTH: 315
<212> TYPE: DNA
<213> ORGANISM: Rift Valley fever virus
<220> FEATURE:
<221> NAME/KEY: misc_structure
<222> LOCATION: (1)..(57)
<223> OTHER INFORMATION: Transmembrane Domain
<220> FEATURE:
<221> NAME/KEY: misc_structure
<222> LOCATION: (58)..(315)
<223> OTHER INFORMATION: Cytosolic Domain

<400> SEQUENCE: 7
tttgttgttg tgtttgtatt cagttctatt gcaataattt gtttagctat tctttatagg      60
gtgcttaagt gcctgaagat tgccccaagg aaagttctga atccactaat gtggatcaca     120
gccttcatca gatggatata taagaagatg gttgccagag tggcagacaa cattaatcaa     180
gtgaacaggg aaataggatg gatggaagga ggtcagttgg ttctagggaa ccctgcccct     240
attcctcgtc atgccccaat cccacgttat agcacatacc tgatgttatt attgattgtc     300
tcatatgcat cagca                                                      315

<210> SEQ ID NO 8
<211> LENGTH: 244
<212> TYPE: PRT
<213> ORGANISM: Rift Valley fever virus
<220> FEATURE:
<221> NAME/KEY: mat_peptide
<222> LOCATION: (1)..(244)
<223> OTHER INFORMATION: N Protein

<400> SEQUENCE: 8

Met Asp Asn Tyr Gln Glu Leu Ala Ile Gln Phe Ala Ala Gln Ala Val
1               5                   10                  15

Asp Arg Asn Glu Ile Glu Gln Trp Val Arg Glu Phe Ala Tyr Gln Gly
            20                  25                  30

Phe Asp Ala Arg Arg Val Ile Glu Leu Leu Lys Gln Tyr Gly Gly Ala
        35                  40                  45

Asp Trp Glu Lys Asp Ala Lys Lys Met Ile Val Leu Ala Leu Thr Arg
    50                  55                  60

Gly Asn Lys Pro Arg Arg Met Met Met Lys Met Ser Lys Glu Gly Lys
65                  70                  75                  80

Ala Thr Val Glu Ala Leu Ile Asn Lys Tyr Lys Leu Lys Glu Gly Asn
                85                  90                  95

Pro Ser Arg Asp Glu Leu Thr Leu Ser Arg Val Ala Ala Ala Leu Ala
            100                 105                 110

Gly Trp Thr Cys Gln Ala Leu Val Val Leu Ser Glu Trp Leu Pro Val
        115                 120                 125

Thr Gly Thr Thr Met Asp Gly Leu Ser Pro Ala Tyr Pro Arg His Met
    130                 135                 140

Met His Pro Ser Phe Ala Gly Met Val Asp Pro Ser Leu Pro Gly Asp
145                 150                 155                 160

Tyr Leu Arg Ala Ile Leu Asp Ala His Ser Leu Tyr Leu Leu Gln Phe
                165                 170                 175

Ser Arg Val Ile Asn Pro Asn Leu Arg Gly Arg Thr Lys Glu Glu Val
            180                 185                 190

```
Ala Ala Thr Phe Thr Gln Pro Met Asn Ala Ala Val Asn Ser Asn Phe
            195                 200                 205

Ile Ser His Glu Lys Arg Arg Glu Phe Leu Lys Ala Phe Gly Leu Val
210                 215                 220

Asp Ser Asn Gly Pro Ser Ala Ala Val Met Ala Ala Gln Ala Tyr
225                 230                 235                 240

Lys Thr Ala Ala

<210> SEQ ID NO 9
<211> LENGTH: 265
<212> TYPE: PRT
<213> ORGANISM: Rift Valley fever virus
<220> FEATURE:
<221> NAME/KEY: mat_peptide
<222> LOCATION: (1)..(265)
<223> OTHER INFORMATION: NSs Protein

<400> SEQUENCE: 9

Met Asp Tyr Phe Pro Val Ile Ser Val Asp Leu Gln Ser Gly Arg Arg
1               5                   10                  15

Val Val Ser Val Glu Tyr Phe Arg Gly Asp Gly Pro Pro Arg Ile Pro
            20                  25                  30

Tyr Ser Met Val Gly Pro Cys Cys Val Phe Leu Met His His Arg Pro
        35                  40                  45

Ser His Glu Val Arg Leu Arg Phe Ser Asp Phe Tyr Asn Val Gly Glu
    50                  55                  60

Phe Pro Tyr Arg Val Gly Leu Gly Asp Phe Ala Ser Asn Val Ala Pro
65                  70                  75                  80

Pro Pro Ala Lys Pro Phe Gln Arg Leu Ile Asp Leu Ile Gly His Met
                85                  90                  95

Thr Leu Ser Asp Phe Thr Arg Phe Pro Asn Leu Lys Glu Ala Ile Ser
            100                 105                 110

Trp Pro Leu Gly Glu Pro Ser Leu Ala Phe Phe Asp Leu Ser Ser Thr
        115                 120                 125

Arg Val His Arg Asn Asp Asp Ile Arg Arg Asp Gln Ile Ala Thr Leu
130                 135                 140

Ala Met Arg Ser Cys Lys Ile Thr Asn Asp Leu Glu Asp Ser Phe Val
145                 150                 155                 160

Gly Leu His Arg Met Ile Ala Thr Glu Ala Ile Leu Arg Gly Ile Asp
                165                 170                 175

Leu Cys Leu Leu Pro Gly Phe Asp Leu Met Tyr Glu Val Ala His Val
            180                 185                 190

Gln Cys Val Arg Leu Leu Gln Ala Ala Lys Glu Asp Ile Ser Asn Ala
        195                 200                 205

Val Val Pro Asn Ser Ala Leu Ile Val Leu Met Glu Glu Ser Leu Met
    210                 215                 220

Leu Arg Ser Ser Leu Pro Ser Met Met Gly Arg Asn Asn Trp Ile Pro
225                 230                 235                 240

Val Ile Pro Pro Ile Pro Asp Val Glu Met Glu Ser Glu Glu Glu Ser
                245                 250                 255

Asp Asp Asp Gly Phe Val Glu Val Asp
                260                 265

<210> SEQ ID NO 10
<211> LENGTH: 115
<212> TYPE: PRT
```

```
<213> ORGANISM: Rift Valley fever virus
<220> FEATURE:
<221> NAME/KEY: mat_peptide
<222> LOCATION: (1)..(115)
<223> OTHER INFORMATION: NSm Protein

<400> SEQUENCE: 10

Met Ile Glu Gly Ala Trp Asp Ser Leu Arg Glu Glu Met Pro Glu
1               5                   10                  15

Glu Leu Ser Cys Ser Ile Ser Gly Ile Arg Glu Val Lys Thr Ser Ser
            20                  25                  30

Gln Glu Leu Tyr Arg Ala Leu Lys Ala Ile Ile Ala Ala Asp Gly Leu
        35                  40                  45

Asn Asn Ile Thr Cys His Gly Lys Asp Pro Glu Asp Lys Ile Ser Leu
50                  55                  60

Ile Lys Gly Pro Pro His Lys Leu Arg Val Gly Ile Val Arg Cys Glu
65                  70                  75                  80

Arg Arg Arg Asp Ala Lys Gln Ile Gly Arg Glu Thr Met Ala Gly Ile
                85                  90                  95

Ala Met Thr Val Leu Pro Ala Leu Ala Val Phe Ala Leu Ala Pro Val
            100                 105                 110

Val Phe Ala
        115

<210> SEQ ID NO 11
<211> LENGTH: 32
<212> TYPE: DNA
<213> ORGANISM: Artificial Sequence
<220> FEATURE:
<223> OTHER INFORMATION: Forawrd Primer N cds

<400> SEQUENCE: 11
caccatggac aactatcaag accttgcgat cc                              32

<210> SEQ ID NO 12
<211> LENGTH: 25
<212> TYPE: DNA
<213> ORGANISM: Artificial Sequence
<220> FEATURE:
<223> OTHER INFORMATION: Reverse Primer N cds

<400> SEQUENCE: 12
ggctgctgtc ttgtaagcct gagcg                                      25

<210> SEQ ID NO 13
<211> LENGTH: 37
<212> TYPE: DNA
<213> ORGANISM: Artificial Sequence
<220> FEATURE:
<223> OTHER INFORMATION: Forward Primer NSs cds

<400> SEQUENCE: 13
caccatggat tactttcctg tgatatctgt tgatttg                         37

<210> SEQ ID NO 14
<211> LENGTH: 34
<212> TYPE: DNA
<213> ORGANISM: Artificial Sequence
<220> FEATURE:
<223> OTHER INFORMATION: Reverse Primer NSs cds

<400> SEQUENCE: 14
atcaacctca acaaatccat catcatcact ctcc                            34
```

<210> SEQ ID NO 15
<211> LENGTH: 27
<212> TYPE: DNA
<213> ORGANISM: Artificial Sequence
<220> FEATURE:
<223> OTHER INFORMATION: Forward Primer NSm cds

<400> SEQUENCE: 15
caccatgatt gaaggagctt gggattc                                27

<210> SEQ ID NO 16
<211> LENGTH: 24
<212> TYPE: DNA
<213> ORGANISM: Artificial Sequence
<220> FEATURE:
<223> OTHER INFORMATION: Reverse Primer NSm cds

<400> SEQUENCE: 16
agcaaaaaca acaggtgcca aagc                                   24

<210> SEQ ID NO 17
<211> LENGTH: 26
<212> TYPE: DNA
<213> ORGANISM: Artificial Sequence
<220> FEATURE:
<223> OTHER INFORMATION: Forward Primer Gne or Gc cds

<400> SEQUENCE: 17
caccatgaca gtccttccag ccttag                                 26

<210> SEQ ID NO 18
<211> LENGTH: 24
<212> TYPE: DNA
<213> ORGANISM: Artificial Sequence
<220> FEATURE:
<223> OTHER INFORMATION: Reverse Primer Gne cds

<400> SEQUENCE: 18
ggcactgaga gcagtgtgac actg                                   24

<210> SEQ ID NO 19
<211> LENGTH: 24
<212> TYPE: DNA
<213> ORGANISM: Artificial Sequence
<220> FEATURE:
<223> OTHER INFORMATION: Reverse Primer Gc cds

<400> SEQUENCE: 19
tgaggccttc ttagtggcag caag                                   24

<210> SEQ ID NO 20
<211> LENGTH: 23
<212> TYPE: DNA
<213> ORGANISM: Artificial Sequence
<220> FEATURE:
<223> OTHER INFORMATION: Forward Primer M13 Sequencing Primer

<400> SEQUENCE: 20
cccagtcacg acgttgtaaa acg                                    23

<210> SEQ ID NO 21
<211> LENGTH: 23
<212> TYPE: DNA
<213> ORGANISM: Artificial Sequence
<220> FEATURE:

```
<223> OTHER INFORMATION: Reverse Primer M13 Sequencing Primer

<400> SEQUENCE: 21
agcggataac aatttcacac agg                                            23
```

RIFT VALLEY FEVER VIRUS GLYCOPROTEINS, GN AND GC, AND THEIR USE

CROSS REFERENCE TO RELATED APPLICATION

This application claims benefit under 35 U.S.C. §119(e) to U.S. Provisional Application No. 61/757,538, filed Jan. 28, 2013, and U.S. Provisional Application No. 61/916,784, filed Dec. 16, 2013, each of which is incorporated by reference herein in their entireties.

This work was made with Governmental support under grant number 2010-ST0-AG0001 awarded by the Department of Homeland Security Center of Excellence for Emerging and Zoonotic Animal Diseases. The government has certain rights in the invention.

BACKGROUND OF THE INVENTION

Field of the Invention

The present invention relates generally to immunoreagents, and more specifically to Rift Valley fever Virus (RVFV) glycoproteins and their use as vaccine components and as moieties for disease diagnosis and detection, including methods of using such glycoproteins.

Background Information

Rift Valley fever virus (RVFV) is a mosquito-borne zoonotic pathogen that causes high morbidity and mortality in both livestock and humans. The virus has caused outbreaks in ruminants and humans in Africa and the Arabian Peninsula and is classified as a select agent and risk group-3 pathogen by the Centers for Disease Control and Prevention (CDC) and the United States department of Agriculture (USDA).

In ruminant livestock, Rift Valley fever (RVF) is characterized by high mortality in young animals, notably in lambs, fetal malformations and widespread abortion storms; sheep are the most susceptible, with neonatal mortalities approaching 100%. Human infections are often characterized by benign fever but in small proportion of individuals could lead to more serious complications such as retinitis, encephalitis, neurological disorders, hepatic necrosis, or fatal hemorrhagic fever. Although human fatal hemorrhagic cases have been historically estimated at 2% in infected individuals, case fatality rates have increased significantly in recent years as high as 20% including the recent outbreak in Mauritania.

There is increasing demand for sensitive and safe diagnostic tests and efficacious vaccines for zoonotic pathogens, including RVFV, to protect human and animal health. The recent spread of RVFV beyond its traditional endemic boundaries in Africa to the Arabian Peninsula (Jupp and Cornet 1988, Abdo-Salem, et al. 2011, Ikegami and Makino 2009) has resulted in increased interest for RVFV vaccines, rapid diagnostics and associated immunoreagents.

RVFV belongs to the genus *Phlebovirus* within the family Bunyaviridae, which includes over 350 named isolates. It has a tripartite single-stranded RNA genome of negative polarity consisting of small (S), medium (M) and large (L) RNA segments. The M segment encodes for the two structural glycoproteins, Gn/Gc, the 78-kDa protein and the non-structural protein, NSm; and the S segment for the nucleocapsid protein (N) protein and the non-structural protein, NSs. The L-segment encodes for the RNA-dependent RNA polymerase. The N and L proteins are required for viral RNA synthesis; and the NSs protein is the major virulence factor and has been shown to inhibit host transcriptional immune response through generalized transcription downregulation including repression of IFN-β and degradation of protein kinase R. The NSm protein functions to suppress virus-induced apoptosis. The glycoproteins, Gn and Gc, are surface proteins that play a role in virus attachment to initiate infection and have been shown to carry epitopes that elicit the production of neutralizing antibodies, a correlate of protective immunity.

The nucleocapsid (N) protein is the most abundant and highly immunogenic component of the RVF virion and has been used for development of diagnostic assays for detection of RVFV specific antibodies in human and animal sera. Although the N protein is shown to be highly conserved among members of the Bunyaviridae family, a previous indirect ELISA based on the recombinant protein did not show cross-reactivity with other African *phleboviruses* that could hamper the reliability of using this protein in assays for serodiagnosis of RVFV infection. However, the N protein did show serological cross-reactivity with an unidentified agent among some sear from US and Canadian sheep.

There are currently no RVFV vaccines fully approved for use outside its endemic area in Africa and the Arabian Peninsula. Given the potential for viral spread elsewhere including the mainland US, there is an urgent need for a safe and efficacious vaccine. Attributes essential for a vaccine for use in non-endemic areas include safety and the ability to generate a rapid (with primary vaccination) protective immune response in a susceptible host. At present, RVFV in endemic regions is controlled in livestock using live-attenuated Smithburn strain or inactivated whole virus. The Smithburn vaccine is highly immunogenic but is teratogenic in pregnant sheep and cattle. The whole-virus formalin inactivated vaccines are safe but less immunogenic. Other live-vaccine candidates under evaluation are Clone 13 (licensed for use in South Africa), a natural attenuated isolate from a benign RVF case in the Central African Republic, and MP12, a chemically attenuated virus derived from ZH548, an Egyptian wild-type isolate. The immunogenicity and pathogenicity of these candidate vaccines have been evaluated in various animal species; and although both vaccine candidates showed promising results, the MP12 induced fetal malformations during the first trimester. However, a recent study reported the absence of fetal malformations in pregnant ewes inoculated with the virus. Strategies to develop RVFV vaccines include subunit, DNA, virus-like particles, virus replicon particles, virus-vectored, modified live vaccines using reverse genetic engineering, live attenuated, and inactivated whole virus vaccines.

Although some of these vaccines have shown promising results, their immunogenicity and efficacy have either not been determined in a natural host species or have not been shown to induce protective neutralizing antibody titer in single immunization. On the other hand, production of live-vaccines requires high level of biosafety; and their use is associated with potential side effects. Therefore, the general availability of a safe, inexpensive vaccine with DIVA compatibility will be extremely valuable to non-endemic countries outside Africa including the US.

At the present, diagnosis of RVFV infection is achieved using various techniques including virus isolation, antigen detection, nucleic acid amplification techniques, and detection of RVFV specific antibodies. The use of virus isolation is not user-friendly, takes an extended period of time and is also unsafe for laboratory personnel; antigen or nucleic acid detection in the blood of animals only works in cases of host viremia, which in the case of RVFV infection, is a narrow viremic window, lasting on average about 3 days.

The classical methods for detection of antibodies to RVFV include various forms of virus neutralization and haemagglutination inhibition tests. Disadvantages of these techniques include health risk to laboratory personnel, as well as restrictions to high biocontainment laboratories for their use outside RVF endemic areas. On the other hand, application of ELISA to detect IgG antibody to RVFV relied largely on the use of inactivated whole virus lysate, which is also associated with potential health risks.

What is needed are potent virus neutralizing antibody response inducers as efficacious vaccines against RVFV, including immunoreagents that may serve as moieties for effective RVFV detection and disease diagnosis.

SUMMARY OF THE INVENTION

The present invention discloses immunoreagents useful in the treatment and diagnosis of Rift Valley Fever viral infection.

In embodiments, an isolated nucleic acid molecule is disclosed including a nucleotide sequence as set forth in SEQ ID NO:1, where the isolated nucleic acid molecule encodes an polypeptide or protein consisting essentially of an amino acid sequence as set forth in SEQ ID NO: 4 or SEQ ID NO:6.

In one aspect, the encoded polypeptide or protein induces neutralizing antibodies against Rift Valley Fever Virus (RVFV) in a subject at primary dose. In a related aspect, the molecule encodes a functional fragment of said encoded polypeptide or protein.

In another aspect, the nucleic acid molecules include SEQ ID NO: 3, SEQ ID NO: 5, functional fragments thereof, and sequences having at least about 90% homology to SEQ ID NO:3 or SEQ ID NO: 5, where the nucleic acid molecule encodes a polypeptide or protein which induces neutralizing antibodies against Rift Valley Fever Virus in a subject at primary dose.

In one aspect, the nucleic acid molecule further has one or more regulatory nucleic acid sequences including Kozak sequences, promoter sequences, transcriptional enhancers, polyadenylation sites, TATA boxes, initiators, CpG Islands, promoter proximal elements, operons, and combinations thereof.

In another embodiment, a host cell is disclosed containing the above nucleic acid, where the host cell includes a mammalian cell, a bacterial cell, a yeast cell, or an insect cell.

In embodiments, a vector is disclosed containing the above nucleic acid, where the vector functions in a mammalian cell, a bacterial cell, a yeast cell, an insect cell or shuttles function between the cells.

In embodiments, an isolated protein or polypeptide is disclosed including an amino acid sequence as set forth in SEQ ID NO:4, SEQ ID NO:6, an amino acid sequence having at least 90% homology to SEQ ID NO:4 or SEQ ID NO:6, or a function fragment of SEQ ID NO:4 or SEQ ID NO:6, where the polypeptide or protein does not contain a transmembrane domain, and where the protein or polypeptide induces neutralizing antibodies against Rift Valley Fever Virus in a subject a primary dose.

In one aspect, a Rift Valley Fever Virus (RVFV)-specific immunoreagent is disclosed which binds to the above isolated polypeptide or protein. In a related aspect, the immunoreagent includes a monoclonal antibody, antibody form polyclonal sera, Fab, F(ab')2, and Fv fragments. In a further related aspect, the monoclonal antibody or the antibody from polyclonal sera is a neutralizing antibody.

In embodiments, a method of vaccinating a subject in need thereof is disclosed including administering an immunogenically effective amount of a composition comprising an isolated protein or polypeptide comprising an amino acid sequence as set forth in SEQ ID NO:4, SEQ ID NO:6, an amino acid sequence having at least 90% homology to SEQ ID NO:4 or SEQ ID NO:6, or a functional fragment of SEQ ID NO:4 or SEQ ID NO:6, wherein said polypeptide or protein does not contain a transmembrane domain, and wherein said protein or polypeptide induces neutralizing antibodies against Rift Valley Fever Virus in a subject at primary dose. In a related aspect, the subject is a ruminant animal. In another related aspect, the composition further includes an adjuvant. In another related aspect, the composition further comprises a carrier and pharmaceutical excipient. In a further related aspect, administration is via parenteral injection, topical application or airway surface.

In another embodiment, a method for diagnosing Rift Valley Fever (RVF) in a subject is disclosed including contacting a first sample from the subject with a first protein or polypeptide, where the first protein or polypeptide is the above isolated protein or polypeptide; contacting a second sample from the subject with a second protein or polypeptide comprising an amino acid as set forth in SEQ ID NO:8, SEQ ID NO:9, or SEQ ID NO:10, a protein or polypeptide having at least 90% homology to an amino acid as set forth in SEQ ID NO:8, SEQ ID NO:9, or SEQ ID NO:10; or a functional fragment comprising an amino acid sequence as set forth in SEQ ID NO:8, SEQ ID NO:9, or SEQ ID NO:10; and detecting immune complex formation in the first and second samples, where detection of immune complexes in the first and second samples correlates with the presence of RVF viral infection.

In one aspect, detection of immune complexes in only the first sample correlates with exposure of the subject to a vaccine comprising the first protein or polypeptide. In another aspect, failure to detect immune complexes in either the first of second sample correlates with lack of exposure of the subject to RVF virus or vaccine comprising the first protein or polypeptide.

In embodiments, a kit is disclosed including an isolated protein or polypeptide comprising an amino acid sequence as set forth in SEQ ID NO:4, SEQ ID NO:6, an amino acid sequence having at least 90% homology to an amino acid sequence as set forth in SEQ ID NO:4, or SEQ ID NO:6, or a functional fragment of an amino acid as set forth in SEQ ID NO:4, or SEQ ID NO:6, where the polypeptide or protein does not contain a transmembrane domain, and where the protein or polypeptide induces neutralizing antibodies against Rift Valley Fever Virus in a subject at primary dose; a first Rift Valley Fever Virus (RVFV)-specific immunoreagent which binds to the above isolated polypeptide or protein, where the immunoreagent includes monoclonal antibody, antibody from polyclonal sera, Fab, F(ab')2, and Fv fragments; optionally, a second protein or polypeptide comprising an amino acid sequence as set forth in SEQ ID NO:8, SEQ ID NO:9, or SEQ ID NO:10, an amino acid sequence having at least 90% homology to SEQ ID NO:8, SEQ ID NO:9, or SEQ ID NO:10, or a functional fragment of an amino acid sequence as set forth in SEQ ID NO:8, SEQ ID NO:9, or SEQ ID NO:10; optionally, a second RVFV-specific immunoreagent including monoclonal antibody, antibody from polyclonal sera, Fab, F(ab')2, and Fv fragment, which second RVFV-specific immunoreagent specifically binds to the second protein or polypeptide; a container; one or more buffers; and instructions.

BRIEF DESCRIPTION OF THE DRAWINGS

FIG. 6 shows the immunoreactivity of antisera obtained from sheep vaccinated with recombinant RVFV Gn and Gc proteins. There is specific reactivity of the immune sera with Gn and Gc showing the estimated 52 kDa and 60 kDa bands, respectively (arrows), for sheep #169, 170, 163. The recombinant RVFV N protein shows no specific reactivity with the any of immune sera. A positive control showing specific reactivity (31 kDa) of the recombinant N protein with antisera obtained from sheep infected with MP12 RVFV strain.

DETAILED DESCRIPTION OF THE INVENTION

Figure 1:
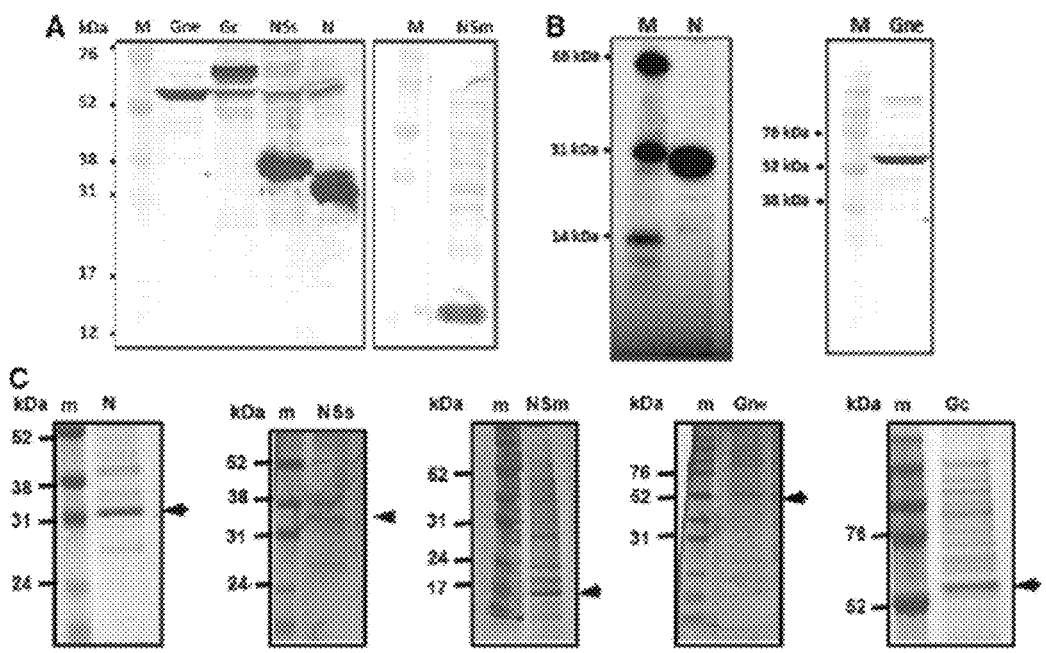
FIG. 1 shows electrophoretograms of baculovirus-expressed Rift Valley fever virus proteins. Proteins were purified and detected using anti-His(C-term)HRP monoclonal antibody. Gn=54 kDa; Gc=60 kDa; NSs=34 kDa; N=32 kDa; NSm=14 kDa; M=marker(A). Monoclonal antibodies against N and Gn, IDE8 and 4D4, respectively, were used to confirm expression of the respective proteins (B). A coomassie blue staining of the purified proteins (C). N=nucleoprotein; NSs=non-structural protein S segment; NSm=non-structural protein m segment; Gn=N-terminus glycoprotein; Gc=C-terminus glycoprotein; M=Molecular weight marker.

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a nucleic acid" includes one or more nucleic acids, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

As used herein, "about," "approximately," "substantially" and "significantly" will be understood by a person of ordinary skill in the art and will vary in some extent depending on the context in which they are used. If there are uses of the term which are not clear to persons of ordinary skill in the art given the context in which it is used, "about" and "approximately" will means plus or minus <10% of particular term and "substantially" and "significantly" will mean plus or minus >10% of the particular term.

The term "isolated" when used in relation to a nucleic acid or amino acid, refers to a sequence that is identified and separated from at least one contaminant nucleic acid with which it is ordinarily associated in its natural environment. That is, an isolated nucleic acid is one that is present in a form or setting that is different from that in which it is found in nature. Isolated sequences also include sequences that have been modified (e.g., via addition or deletion) and synthesized/expressed.

With respect to the RVFV nucleic acids and proteins, references to "functional characteristics" refer to the immunogenicity and/or antigenicity of the sequence.

The terms "fragment," "derivative" and "homologue" when referring to the polypeptides according to the present invention, means a polypeptide which retains essentially the same biological function or activity as said polypeptide, that is, act as an antigenic determinant and/or provide treatment for and/or protection against RVFV infections. Such fragments, derivatives and homologues can be chosen based on the ability to retain one or more of the biological activities of a RVFV polypeptide, that is, act as an antigenic determinant and/or provide treatment for and/or protection against RVFV infections. The polypeptide vaccines of the present invention may be recombinant polypeptides, natural polypeptides or synthetic polypeptides.

An "antigenic determinant" is, unless otherwise indicated, a molecule that is able to elicit an immune response in a particular animal or species. Antigenic determinants include proteinaceous molecules, i.e., polyaminoacid sequences, polypeptides, fragments, derivatives or variants that may include other moieties, for example, carbohydrate moieties, such as glycans, and/or lipid moieties.

"N" as used herein refers to a nucleocapsid protein or polypeptide of RVFV. The term "N" as used herein also includes fragment, derivatives or homologs thereof that may provide cross-reactivity with RVFV strains. The sequence as disclosed herein is represented by SEQ ID NO:8, NSs and NSm represent two non-structural proteins, and are represented as SEQ ID NO:9 and SEQ ID NO:10, respectively.

"Gn" as used herein refers to a structural protein of RVFV, which contains a C-terminal Golgi localization signal. The term "Gn" as used herein also includes fragment, derivatives or homologs thereof that may provide cross-reactivity with RVFV strains, and is represented as SEQ ID NO:4 herein.

The term "Gc" as used herein refers to a protein of RVFV that harbors a C-terminal lysine-based ER retention signal, and is represented as SEQ ID NO:6 herein.

As used herein, the ectodomain of the Gn protein has a Mw of approximately 54 kDa. Also, as part of the instant disclosure are modification of the sequence comprising the ectodomain of Gn that result in the glycosylation of that protein (see SEQ ID NO:4). For example, fusion of Gn with Gc will form a fusion polypeptide comprising additional glycosylation sites.

The transmembrane domain and cytoplasmic tail of the Gn as disclosed herein are represented by the nucleic acid sequence as set forth in SEQ ID NO:7.

As used herein "consisting essentially of" means containing the specific component and those components that do not materially affect the basic and novel characteristics of a composition (e.g., addition of $(His)_n$ amino acids at the end of a polypeptide or protein, where n is an integer from 1 to 6, would represent a composition consisting essentially of the polypeptide or protein).

As used herein "primary dose" means the first administration of an immunoreagent (e.g., antigen or vaccine) to a subject, as opposed to a secondary or "booster" dose, where the latter is an extra administration of a vaccine after the primary dose. For example, neutralizing antibodies produced within the first 14 days after vaccination would be associated with primary dose.

As used herein, "Rift Valley Fever Virus-specific immunoreagent" means a proteinaceous moiety which specifically binds to RVFV viral components and which exhibits substantially no cross-reactivity with non-RVFV viral components.

The phrase "biological sample" refers to a fluid or tissue of a mammal (e.g., ruminants such as cattle, goats, sheep, giraffes, yaks, deer, camels, llamas, antelope, and the like) that commonly contains antibodies or viral particles. Such components are known in the art and include, without limitation, blood, plasma, serum, spinal fluid, lymph fluid, secretions of the respiratory, intestinal or genitourinary tracts, tears, saliva, milk, white blood cells, and myelomas.

As used here, "ADP" means an antigenic determinant-containing polypeptide (e.g., N, Gn, Gc, NSs, or NSm of RVFV).

As used herein, an "antibody" is defined in terms consistent with that recognized within the art: they are multi-subunit proteins produced by a mammalian organism in response to an antigen challenge. The antibodies of the present invention include monoclonal antibodies and polyclonal antibodies, as well as fragments of such antibodies, including, but not limited to, Fab or F(ab')2, and Fv fragments.

As used herein, the term "subunit" refers to a portion of the RVFV which is itself antigenic, i.e., capable of inducing an immune response in an animal. The term should be construed to include subunits which are obtained by both recombinant and biochemical methods.

As used herein, the term "multivalent" means a vaccine containing more than one isolate from the RVFV, whether from the same species (i.e., different isolates of RVFV) or from a different RVFV. Even for a given genus and species of RVFV each isolate may share some antigens with other isolates (i.e., "common" antigens), while other antigens will be unique to that isolate. Because a multivalent vaccine provides a greater variety of antigens to the host's immune system, the immune response stimulated in the host is broader than that stimulated by only a single isolate.

As used herein, the term "isolate" refers to a virus obtained from a specific source. Isolate is used interchangeably with the term "strain".

As used herein, the term "virulent" mans an isolate that retains its ability to be infectious in an animal host.

As used herein, the term "inactivated" means a vaccine containing an infectious organism that is no longer capable of replication and/or growth.

As used herein, the term "RVFV" as sued herein refers to all viruses belonging to species RVFV in the genus *Phlebovirus* within the family Bunyaviridae.

As used herein, the term "vaccine" as used herein refers to a pharmaceutical composition comprising at least one immunologically antigenic determinant that induces an immunological response in an animal and possibly, but not necessarily, one or more additional components that enhance the immunological activity of said determinant. A vaccine may additionally comprise further components typical to pharmaceutical compositions. The immunologically active component of a vaccine may comprise complete live virus in either its original form or as attenuated virus in a so-called modified live vaccine or virus inactivated by appropriate methods in a so-called killed vaccine. In another form, the immunologically active component of a vaccine may comprise appropriate elements of said viruses (subunit vaccines) whereby these elements are generated either by destroying the whole organism or the growth cultures of such viruses and subsequent purification steps yielding in the desired structure(s), or by synthetic processes induced by an appropriate manipulation of a suitable system such as, but not restricted to, bacteria, insects, mammalian, or other species, plus subsequent isolation and purification procedures or by induction of said synthetic processes in the animal needing a vaccine by direct incorporation of genetic material using suitable pharmaceutical compositions (polynucleotide vaccination). A vaccine may comprise one or simultaneously more than one of the elements described above. In embodiments, the vaccine may contain components from the host cell expressing the subunits. In one aspect, the vaccine may contain Sf9 components from a lysate.

The terms "protecting", "protection", "protective immunity" or "protective immune response," as used herein, are intended to mean that the host ruminant mounts an active immune response to the vaccine or polypeptides of the present disclosure, such that upon subsequent exposure to the virus or a virulent viral challenge, the ruminant is able to combat the infection. Thus, a protective immune response will decrease the incidence of morbidity and mortality from subsequent exposure to the virus among host ruminants. Those skilled in the art will understand that in a commercial ruminant setting, the production of a protective immune response may be assessed by evaluating the effects of vaccination on the herd as a whole, e.g., there may still be morbidity and mortality in a minority of vaccinated ruminants.

As used herein, the term "live virus" refers to a virus that retains the ability of infecting an appropriate subject (as opposed to inactivated (killed) or subunit vaccines).

As used herein, the term "immunogenically effective amount" refers to an amount, which is effective in reducing, eliminating, treating, preventing or controlling the symptoms of the RVFV infections, diseases, disorders, or condition.

The impact of RVF outbreaks in Africa and the Arabian Peninsula, and the potential for viral spread to non-endemic areas, makes the development of safe and efficacious vaccines urgent. RVFV is a uniquely suitable candidate for a one-health focused approach to prevent both livestock and human disease through animal vaccinations. However, there are currently no fully licensed vaccines for human or livestock use outside endemic areas, despite numerous potential vaccine candidates. Essential attributes for a RVFV vaccine for human or veterinary use include safety and high immunogenicity, and the ability to induce a rapid onset of protective response with single vaccination, at most within two weeks of administration in susceptible host species; and, in addition, should be DIVA compatible.

Herein, the immunogenicity of a recombinant baculovirus-expressed RVFV Gn and Gc glycoprotein-based vaccine candidate in a target species, the sheep, is disclose. Gn and Gc are presented as glycosylated proteins on the surface of RVF virions and had been shown to carry epitopes that elicit neutralizing antibodies, the only established correlate of protective immunity against virus infection.

Gn and Gc are also utilized by the virus for attachment to target cells. Thus, these surface glycoproteins represent ideal targets for vaccine development; and, while not being bound by theory, antibodies targeting epitopes on both structural glycoproteins may generate a potent virus neutralizing effect.

In embodiments, vaccine immunogens, Gn and Gc, may be produced using expression constructs designed to include a signal peptide at their N-terminus, including a unique signal peptidase cleavage site that ensures (a) processing through translocation into the ER and cellular glycosylation pathway and (b) enhances protein expression.

For example, as shown herein, sheep were immunized with purified baculovirus-expressed Gn and Gc proteins adjuvanted with montanide ISA25, resulting in induction of strong virus neutralizing antibody response in all vaccinated animals. The vaccine induced protective, (i.e. ≥1:40), virus neutralizing titers with single vaccination in five of the six animals within two weeks post vaccination. These results compared favorably with the outcome recently reported vaccinations using vaccines based on RVFV glycoproteins, such as GnGc-VLPs and Gn-ectomain as well as a Newcastle Disease virus-vectored vaccine (NDFL-GnGc) and virus replicon particles that have shown to elicit neutralizing antibodies in immunized animals. For example, results of neutralizing antibody response induced by a GnGc-VLP and Gn-ectodomain vaccine are based on the mouse model, in which the Gn-ectodomain vaccine required two vaccinations to induce seroconversion. The Gn-ectodomain elicited neutralizing antibodies in only four out of six sheep at about three weeks post vaccination; similarly, the NDFL-GnGc also required two vaccinations to induce neutralizing antibodies. In contrast, the GnGc-based recombinant protein vaccine as disclosed herein induced protective neutralizing antibody titers in 80% (5/6) of sheep within two weeks of vaccination and 100% (6/6) sheep at three weeks pv.

While not being bound by theory, the robust neutralizing antibody response elicited by the RVFV vaccine as disclosed herein could be attributed to the concurrent use of Gn and Gc proteins as vaccine immunogens. Gn is known to contain virus neutralizing epitopes; however, includes of Gc in the vaccine is suggested to provide an additional target for neutralizing antibodies. Importantly, neutralizing antibody titers increased sharply in all animals following the booster dose, and this high anamnestic response was maintained in all animals for more than three weeks. As disclosed herein, early-onset vaccine-induced IgG antibody response to Gn occurred in half of the sheep within seven days pv followed by seroconversion in 100% of the animals at two weeks pv for both Gn and Gc. Taken together, these results support the conclusion that the RVFV recombinant GnGc glycoprotein-based vaccine candidate is highly immunogenic, eliciting strong immune response in the sheep, the most susceptible target species to RVFV infection.

Differentiating infected from vaccinated animals (DIVA) during RVF disease outbreaks is of fundamental epidemiological importance. Therefore, DIVA compatibility of a vaccine with accompanying diagnostic tests represents an important factor to be considered when designing vaccines especially for use in countries or regions non-endemic for RVFV. Using the RVFV glycoproteins and the nucleocapsid protein as diagnostic antigens, it is possible to distinguish vaccine-induced antibody responses from RVFV MP12 infection in sheep. The increase in international trade in livestock coupled with the potential for RVFV outbreaks in non-endemic areas provides strong incentives for the development of DIVA vaccines. The absence of the nucleoprotein in the vaccine candidate affords development of a DIVA vaccine with a companion diagnostic assay using a recombinant N and Gn/Gc ELISA.

The N protein represents a suitable diagnostic antigen as it is the most abundant viral protein and is highly immunogenic, inducing antibodies within the first days after infection. Furthermore, the recombinant GnGc glycoprotein subunit vaccine as disclosed elicited strong neutralizing and IgG antibody responses in the natural host, which may be easily detected by ELISA assays. As disclosed herein, analysis of the structural morphology of the vaccine immunogens by electron microscopy confirmed that the proteins, upon reconstitution, formed into clumps or aggregates which were very much distinct from VLPs.

RVFV VLP assembly has been reported to occur by simultaneous production of Gn and Gc by both mammalian and insect cells, as well as in all cases involved the co-expression of nonhistidine-tagged proteins. However, Gn used in the current vaccine formulation was truncated lacking the transmembrane and cytoplasmic domains; and both recombinant proteins (Gn and Gc) carried a hexahistidine tag at their C-terminus.

As supported by the present disclosure, the rapid onset of a strong neutralizing antibody response in the natural host suggests that immunization with a subunit GnGc vaccine may confer protection, within two weeks; a fundamentally important attribute required during outbreaks to prevent viral spread. while not being bound by theory, the fact that RVFV has low genetic diversity and consists of a single serotype suggests that the recombinant Gn and Gc glycoprotein vaccine would likely confer protection against all strains of the virus.

The present disclosure provides isolated nucleic acid and amino acid sequences, methods of using those sequences to create subunit vaccines or other immunogenic compositions, immunoreagents, diagnostic assays, and the like. In embodiments, the disclosure provides an isolated nucleic acid molecule comprising a nucleotide sequence including SEQ ID NO:1, SEQ ID NO:3, SEQ ID NO:5, functional fragments thereof, and sequences having at least 90% homology to any of the foregoing and retaining the functional characteristics thereof.

In embodiments, the disclosure provides an isolated nucleic acid molecule encoding an immunogenic RVFV protein or functional fragment thereof, linked to a signal peptide, where the signal peptide comprises SEQ ID NO:2, functional fragments thereof, or sequences having at least about 90% homology thereto, or is encoded by a nucleic acid sequence comprising SEQ ID NO:1, functional fragments thereof, and sequences having at least about 90% homology thereto and retaining the functional characteristics thereof. Exemplary immunogenic RVFV proteins include Gn, Gc, N, NSs, and/or NSm.

In embodiments, recombinant proteins are also described, which comprise an amino acid sequence including SEQ ID NO:4, SEQ ID NO:6, SEQ ID NO:8, SEQ ID NO:9, SEQ ID NO:10, functional fragments thereof, and sequences having at least about 90% homology to any one of the foregoing, and retaining the functional characteristics thereof. The disclosure also provides signal peptides comprising a sequence including SEQ ID NO:2, functional fragments thereof, sequences having at least about 90% homology thereto, as well as nucleic acid sequences encoding such a peptide, including SEQ ID NO:1, functional fragments thereof, and sequences having at least about 90% homology thereto and retaining the functional characteristics thereof.

Recombinant vaccines comprising the above-mentioned proteins and/or signal peptides as active agents (along with suitable carriers, adjuvants, and the like) are also encompassed by the present disclosure.

As disclosed herein, immunogenic compositions comprising RVFV proteins are described, including methods of inducing an immune response against RVFV using such immunogenic compositions and administering to a subject in need thereof a composition comprising one or more of the above-described proteins or recombinant vectors encoding such proteins.

In embodiments, methods of efficient baculovirus expression of target sequences are also disclosed, including the use of a signal peptide encoded by SEQ ID NO:1 or comprising SEQ ID NO:2, functional fragments thereof, or sequences having at least about 90% homology thereto and retaining the functional characteristics thereof. The signal peptide coding sequence may be attached upstream of the target sequence, and along with a Kozak sequence, may be used to obtain efficient expression in a baculovirus system.

Recombinant proteins provide a safe platform for development of improved diagnostics and in some cases for subunit vaccines. As disclosed herein, a panel of RVFV proteins (N, NSs, NSm, Gn and Gc) using the baculovirus expression system is provided, which proteins serve as diagnostic targets and vaccine components. While not being bound by theory, one of the advantages of using the baculovirus expression system is the ability to scale up expression and allow post-translational protein modification, which in the case of glycoproteins, may enhance antigenicity and immunogenicity.

Gn (N-terminus) and Gc (C-terminus) glycoproteins are surface proteins of Rift Valley fever virus (RVFV), a member of the family Bunyaviridae. The proteins are encoded from the medium (M) segment of the viral genome and have been shown to carry epitopes that elicit production of virus neutralizing antibodies, a correlate for protective immunity. The unmodified forms of Gn and Gc coding sequences do not express efficiently in eukaryotic expression systems and may not be glycosylated, a posttranslational protein modification critical for enhanced antigenicity and immunogenicity. In embodiments, molecular modifications to Gn may be introduced by expressing the coding sequence without the transmembrane domain and the cytosolic region.

Gn and Gc carry 1 and 4 glycosylation sites, respectively. In a related aspect, to ensure that Gn and Gc, are translocated into the ER and glycosylated, a signal peptide sequence carrying a signal peptidase cleavage site upstream of the 5' end of the coding sequence may be added. In a further related aspect, such a modification ensures correct protein trafficking through the lumen of the endoplasmic reticulum (ER) of a eukaryotic expression system. In a further related aspect, sequence modifications made to Gn and Gc result in strong expression, including that Gn protein containing such a modification was present in the periphery of the plasma membrane.

In embodiments, antibody reactivity of the recombinant proteins with RVFV antisera by Western blot and indirect ELISA shows that the proteins are immunoreactive, and while not being bound by theory, this provides a strong indication of correct structural conformation.

As disclosed herein, using MP12 vaccinated and wild type challenged sera, the RVFV nucleocapsid (N) protein was the most reactive. As the most abundant and highly immunogenic structural component of RVFV virion, the N protein has been considered the best choice for the development of immunoreagents for antigen detection assays. The early immune response and strong antibody reactivity against N protein with MP12-vaccinated sera indicates that the N protein could find application in a vaccine product by offering protective immunity to RVFV infection.

As disclosed herein, the glycoprotein Gn also showed an early-response reactivity (day 3 pv) in western blot and ELISA with MP12 vaccinated sera and was detected by day 28 pi sera from all wild type-infected sheep. Further, Gn, in addition to the N-protein, has been identified as a diagnostic antigen. Moreover, the early and specific antibody response to Gn found with MP12 vaccinated sheep makes this protein suitable for a vaccine as well. Importantly, RVFV glycoproteins, Gn and Gc, have been shown to contain epitopes that induce production of neutralizing antibodies, a correlate of protective immunity against RVFV infection.

As disclosed herein, baculovirus-expressed recombinant Gn alone or in combination with recombinant N, may improve the sensitivity and specificity of herd screening for RVFV infections in areas where cross-reactivity with other bunyaviruses/phleboviruses may be an issue. Recombinant Gc also showed strong reactivity with sheep sera but seemed to be less immunogenic when compared with Gn. However, the induction of a strong antibody response to Gc appears later in MP12-vaccinated animals compared to N and Gn. In embodiments, improved RVFV detection may be achieved by using RVFV nucleic acids in parallel with antibody detection to identify early infected ruminants.

In embodiments, the recombinant proteins find application in diagnostic assays or may be used to produce immunoreagents such as monoclonal antibodies, where the latter may be used, inter alia, for diagnostic assays. As disclosed herein, the recombinant proteins also find application as vaccine components against RVFV.

In embodiments, the Gn coding sequence does not contain the transmembrane domain. As such, Gn can be produced easily in Sf9 cells using the baculovirus expression system, whereas full-length Gn may not. Also, fusion of a 54-nucleotide signal peptide sequence (SEQ ID NO:2) to the 5' end of Gn and Gc ensures N-glycosylation of both proteins in an eukaryotic expression system; the unmodified version of the Gn/Gc sequences may not.

The development of a diagnostic tool that differentiates infected from vaccinated animals (DIVA) is very much needed in regions non-endemic for RVFV. While not being bound by theory, the apparent poor immunogenicity of RVFV NSm in ruminant hosts as disclosed herein, makes the use of NSm as a target for developing a DIVA diagnostic test questionable. On the other hand, NSs-specific antibodies were consistently detected in RVFV-infected/vaccinated sheep, which demonstrates that the NSs protein may serve as a candidate for a DIVA diagnostic assay.

Methods for in vitro detection and diagnosis of RVFV infection in a biological sample are also disclosed using the RVFV proteins described herein. In embodiments, the methods may comprise contacting a biological sample with RVFV protein described herein under appropriate conditions which allow reaction of the protein with RVFV-specific antibodies present in the sample, and detecting such reaction in the sample (i.e., detecting the presence of any immune complexes formed in the sample). Alternatively, antibodies may be produced against the RVFV proteins described herein, and used to detect RVFV antigens in a sample. Thus, in embodiments, the disclosure provides an antibody produced against a recombinant RVFV protein described herein. In embodiments, combinations of the above-described proteins are used in a multiplexing assay having increased sensitivity and specificity for screening subjects for RVFV infection.

The recombinant NSs protein as disclosed herein showed early-onset reactivity with MP12 sera, but had an overall lower reactivity than the N protein. While not being bound by theory, this may be attributed to the typically low antibody titres raised against the NSs protein after RVFV infections. the RVFV NSs protein is responsible for general suppression of the host transcriptional machinery including type I interferons. In contrast to NSs, the other non-structural protein NSm, showed poor reactivity with sera from MP12 vaccinated and wild type challenged animals in western blot. Further assessment of its reactivity in ELISA test showed little or no reactivity with MP12 vaccinated sera, demonstrated by extremely low OD values. Sera from 3 sheep (2 wild type-infected, P7 and P10, and 1 MP12 vaccinated, P5), at day 28 pi showed relatively high reactivity when compared to day 0 sera. In a related aspect, in a virulent RVFV challenge experiment using ELISA, seropositivity was detected for NSs antibodies in 3 control sheep, whereas only 2 of the 3 animals were seropositive for NSm; this was the first time immunoreactivity against NSm had been detected in a natural host species (Bird, et al. 2011). Again, while not being bound by theory, this might indicate that NSm is less immunogenic when compared to NSs or is expressed at lower levels resulting in a lower antibody response in mammalian hosts.

Research efforts aimed at the development and validation of a new generation of safe and accurate diagnostic immunoreagents and assays based on RVFV recombinant antigens are critical. In embodiments, expression of several RVFV proteins and assessment of their reactivity against a panel of immune sera from natural hosts is disclosed herein. In a related aspect, analysis of antibody reactivity revealed that the proteins were expressed in the correct conformation in a baculovirus expression system. Addition of a fusion signal peptide sequence to the structural glycoproteins, Gn and Gc, ensured processing of the proteins through the cellular glycosylation pathway, suggesting a prerequisite for their enhanced antigenicity.

In embodiments, baculovirus-expressed N, Gn, Gc and NSs may be utilized as potential serodiagnostic targets for monitoring host humoral immune response to infection and/or vaccination. In one aspect, the immunoreactivity towards NSm was rather weak making this RVFV antigen a less desirable diagnostic target. In another aspect, the general immunoreactivity profile suggests that N and Gn would represent desirable targets for development of highly sensitive serodiagnostic assays.

In embodiments, vaccine formulations may require DIVA compatibility with companion diagnostic DIVA tests. As shown herein, baculovirus-expressed N and NSs assays, depending on the vaccine composition, may be used for such companion assays.

As used herein, a "Rift Valley Fever Virus" or "RVFV" refers to a virus which causes the disease Rift Valley fever, including closely-related variants of these viruses which may have appeared and which will appear in the future.

An unaffected animal is an animal which has either not been exposed to a RVF infectious agent, or which has been exposed to a RVF infectious agent such as RVFV but is not showing symptoms of the disease. An affected animal is one which shows symptoms of RVF or from which RVFV may be isolated.

The terms "treating" or "treatment", as used herein, refer to reduction or alleviation of at least one adverse effect or symptom of RVFV infection.

As used herein, an "ORF" refers to an open reading frame, or polypeptide-encoding segment, isolated from a viral genome, including a RVFV genome. In the present polynucleic acid, an ORF can be included in part (as a fragment) or in whole, and can overlap with the 5'- or 3'-sequence of an adjacent ORF.

A "vector" is any means for the transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. Viral vectors include alphavirus, retrovirus, adeno-associated virus, pox, baculovirus, vaccinia, herpes simplex, Epstein-Barr and adenovirus vectors. Non-viral vectors include, but are not limited to plasmids, liposomes, electrically charged lipids (cytofectins), DNA-protein complexes, and biopolymers. In addition to a nucleic acid, a vector may also contain one or more regulatory regions, and/or selectable markers useful in selecting, measuring, and monitoring nucleic acid transfer results (transfer to which tissues, duration of expression, etc.).

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell.

A cell has been "transformed" by exogenous or heterologous DNA when the transfected DNA effects a phenotype change. The transforming DNA can be integrated (covalently linked) into chromosomal DNA making up the genome of the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

As used herein, a "polypeptide" refers generally to peptides and proteins having more than eight amino acids.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode an antigenic determinant are optimized for expression in a particular host cell (e.g., yeast, mammalian, plant, fungal, and the like) used to produce the enzymes.

As to amino acid sequences, one of skill will recognize that individual substitutions, deletions or additions to a nucleic acid, peptide, polypeptide, or protein sequence which alters, adds or deletes a single acid or a small percentage of amino acids in the encoded sequence is a "conservatively modified variant" referred to herein as a "variant" where the alteration results in the substitution of an amino acid with a chemically similar amino acid. Conservative substitution tables providing functionally similar amino acids are well known in the art. See, for example, Davis et al., "Basic Methods in Molecular Biology" Appleton & Lange, Norwalk, Conn. (1994). Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, 1984, Proteins).

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 86%, 97%, 88%, 89%, 90%, 91%, 92%, 93%, 94%, 95%, 96%, 97%, 98%, 99%, or higher identity over a specified region (e.g., the sequence of an epitope of a Gn protein of RVFV), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to the compliment of a test sequence. The definition also includes sequences that have deletions and/or additions, as well as those that have substitutions. As described below, the preferred algorithms can account for gaps and the like. Preferably, the identity exists over a region that is at least about 25 amino acids or nucleotides in length, or more preferably over a region that is 50-100 amino acids or nucleotides in length.

Sequence homology describes the sequence relationships between two or more nucleic acid or amino acid sequences when aligned for maximum correspondence over a specified comparison window. The percentage of "homology" is determined by comparing two optimally aligned sequences over the comparison window. For "optimal alignment" of the two sequences, it will be appreciated that the portion of the sequence in the comparison window may include gaps (e.g., deletions or additions) as compared to the reference sequence, which does not contain additions or deletions. After alignment, the number of matched positions (i.e., positions where the identical nucleic acid base or amino acid residue occurs in both sequences) is determined and then divided by the total number of positions in the comparison window. This result is then multiplied by 100 to calculate the percentage of homology.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1991, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement).

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions.

Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence. The variant peptides of the present invention may be purified to homogeneity or other degrees of purity. The level of purification will be based on the intended use. The critical feature is that the preparation allows for the desired function of the variant peptide, even if in the presence of considerably amounts of other components.

In some uses, "substantially free of cellular material" includes preparations of the variant peptide having less than about 30% (by dry weight) other proteins (i.e., contaminating protein), less than about 20% other proteins, less than about 10% other proteins, or less than about 5% other proteins. When the variant peptide is recombinantly produced, it can also be substantially free of culture medium, i.e., culture medium represents less than about 20% of the volume of the protein preparation.

The isolated variant proteins can be purified from cells that naturally express it, purified cells that have been altered to express it (recombinant), or synthesized using known protein synthesis methods. For example, a nucleic acid molecule encoding the varinat protein is cloned into an expression vector, the expression vector introduced into a host cell and the variant protein expressed in the host cell. The variant protein can then be isolated from the cells by an appropriate purification scheme using standard protein purification techniques. Many of these techniques are described in detail below.

The proteins of the present disclosure may be attached to heterologous sequences to form chimeric or fusion proteins. Such chimeric and fusion proteins comprise a variant protein operatively linked to a heterologous protein having an amino acid sequence not substantially homologous to the variant protein. "Operatively linked" indicates, for example, that the variant protein and the heterologous protein are fused in-frame. The heterologous protein can be fused to the N-terminus or C-terminus of the variant protein.

A chimeric or fusion protein may be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers Alternatively, PCR amplification of gene fragments may be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A variant protein-encoding nucleic acid can be cloned into such an expression vector such that the fusion moiety is linked in-frame to the variant protein.

Polypeptides sometimes contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in polypeptides are described in basic tests, detailed monographs, and the research literature, and they are well known to those of skill the art. Accordingly, the variant peptides of the present invention also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment or phosphotidylinositol, cross-linking, cyclization, disulfide bond formation, demethylation, formation of covalent crosslinks, formation of cystine, formation of pyroglutamate, formylation, gamma carboxylation, glycosylation, CPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The present disclosure further provides fragments of the variant proteins of the present invention, in addition to proteins and peptides that comprise and consist of such fragments, provided that such fragments act as an antigenic determinant and/or provide treatment for and/or protection against RVFV infections as provided by the present invention.

As used herein, a fragment comprises at least 8 or more contiguous amino acid residues from a RVFV polypeptide or variant protein.

In one embodiment, the present invention relates to a polypeptide comprising a antigenic determinant of RVFV, herein referred to as an antigenic determinant-containing polypeptide (ADP). The polypeptide may be a homologue, a derivative, or a variant of the antigenic determinant, or an immunologically active or a functional fragment thereof. The polypeptide may be isolated, synthesized, or recombinantly expressed using antigenic determinant-encoding nucleic acids described herein.

Examples of antigenic determinants of the present disclosure include but are not limited to the amino acid sequences as set forth in (SEQ ID NOS:4, 6, 8, 9, and 10). These ADPs may be administered as fragments, polypeptides, or proteins having the desired glycosylation of the ectodomain of the Gn according to the immunization protocols described herein.

The present disclosure also provides isolated and/or recombinant nucleic acids that encode a ADP as described herein. According to an embodiment of the invention, the nucleotide sequence of a ADP encodes a neutralizing epitope. In addition, it should be understood based on the general state of the art that other equivalent sequences to the nucleotide or amino acid sequences of the ADPs are covered by the present disclosure. For example, some deletions, insertions and substitutions in the amino acid sequence of the ectodomain of the Gn are covered by the present disclosure, unless such mutation abolishes the ability of the ADP to induce the generation of neutralizing antibody.

The ADP-encoding nucleic acids of the invention are useful for several purposes, including the recombinant expression of the corresponding ADP polypeptides.

Nucleic acids of the invention include those that encode an entire ADP as well as those that encode a subsequence of a ADP polypeptide. for example, the disclosure includes nucleic acids that encode a polypeptide which is not a full-length ADP, but nonetheless has protective antigenic activity against RVFV infection. The invention includes not only nucleic acids that include the nucleotide sequences as set forth herein, but also nucleic acids that are substantially identical to, or substantially complementary to, the exemplified embodiments. For example, the invention includes nucleic acids that include a nucleotide sequence that is at least about 70% identical to one that is set forth herein, at least 75%, at least 80%, at least 85%, at least 90%, and at least about 95% identical to an exemplified nucleotide sequence. The nucleotide sequence may be modified as described herein, so long as the polypeptide encoded is capable of inducing the generation of neutralizing antibodies.

The nucleic acids that encode a ADP polypeptide of the invention may be obtained using methods that are known to those of skill in the art. Suitable nucleic acids (e.g., c DNA, genomic, or subsequences) may be cloned, or amplified by in vitro methods such as the polymerase chain reaction (PCR) using suitable primers, the ligase chain reaction (LCR), the transcription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, Guide to Molecular Cloning Techniques, Methods in Enzymology 1523 Academic Press, Inc., Sand Diego, Calif. (Berger); Sambrook et al. (1989) Molecular Cloning—A Laboratory Manual (2nd ed.) Vol. 1-3, Cold Spring Harbor Laboratory, Cold spring Harbor Press, NY, (Sambrook et al.); Current Protocols in Molecular Biology, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; PCR Protocols A Guide to Methods and Applications (Innis et al., eds) Academic Press Inc. San Diego, Calif. (1990) (Innis); Amheim & Levinson (Oct. 1, 1990) C&EN 36-47; The Journal Of NIH Research (1991) 3: 81-94; (Kwoh et al. (1989) Proc. Natl. Acad. Sci. USA 86: 1173; Guatelli et al. (1990) Proc.

Natl. Acad. Sci. USA 87, 1874; Lomell et al. (1989) J. Clin. Chem., 35: 1826; Landegren et al., (1988) Science 241: 1077-1080; Van Brunt (1990) Biotechnology 8: 291-294; Wu and Wallace (1989) Gene 4: 560; and Barringer et al. (1990) Gene 89: 117. Improved methods of cloning in vitro amplified nucleic acids are described in Wallace et al., U.S. Pat. No. 5,426,039. Nucleic acids that encode the ADP polypeptide of the invention, or subsequences of these nucleic acids, can be prepared by any suitable method as described above, including, for example, cloning and restriction or appropriate sequences.

A nucleic acid encoding an ADP may then be introduced into either a prokaryotic or eukaryotic host cell through the use of a vector, plasmid or construct and the like to produce the ADP polypeptide of the invention. A typical expression cassette contains a promoter operably linked to a nucleic acid that encodes the glycosyltransferase or other enzyme of interest. The expression cassettes are typically included on expression vectors that are introduced into suitable host cells, including for example, bacterial, insect, fungal, plant or animal cells. Either constitutive or regulated promoters can be used in the present invention. Promoters suitable for use in eukaryotic host cells are well known to those of skill in the art. The expression vectors of the invention can be transferred into the chosen host cell by methods known to those of ordinary skill in the art including, for example, calcium phosphate transfection, DEAE-dextran mediated transfection, transvection, microinjection, cationic lipid-mediated transfection, electroporation, transduction, scrape loading, ballistic introduction, infection or other methods (See Molecule Cloning: A Laboratory Manual, 2.sup.nd ed., Vol. 1-3, ed. Sambrook et al., Cold Spring Harbor Laboratory Press (1989)). Transformed cells can be selected, for example, by resistance to antibiotics conferred by genes contained on the plasmids, such as the amp, gpt, neo and hyg genes.

An ADP, homologue, fragments or other derivatives, or variants thereof, or cells expressing it may be used as an antigen to produce antibodies thereto. The present invention includes, for examples monoclonal and polyclonal antibodies, chimeric, single chain, as well as Fab fragments. Thus, the present disclosure also encompasses a method of generating antibodies directed against one or more ADP described above comprising providing a polypeptide of the ADP or a biologically functional homologue or derivative or variant thereof and administering the polypeptide to an animal subject in an amount sufficient to induce an immunological response to generate antibodies directed towards the ADP polypeptide. Thus, the invention includes a method for generating antibodies against an ADP or RVFV.

In embodiments, amino acids as set forth in SEQ ID NO:2 which represent a signal sequence for Gn in RVFV is used in combination with Gc as an ADP. The ADPs as disclosed herein may be administered according to the immunization protocol as described.

In embodiments, the disclosure provides antibodies that selectively bind to the ADP polypeptide, a derivative, a homologue or a variant as well as fragments thereof. Such antibodies may be used to quantitatively or qualitatively detect the ADP or variants as described.

Many methods are known for generating and/or identifying antibodies to a given target peptide, such as an ADP. Several such methods are described by Harlow, Antibodies, Cold Spring Harbor Press, (1989). The full-length ADP, derivative, homologue or variant or fragments or a fusion protein may be used.

For preparation of monoclonal antibodies, any technique known in the art which provides antibodies produced by continuous cell line cultures can be used. Examples include various techniques, such as those in Kohler, G. and Milstein, C., Nature 256:495-497 (1975); Kozbor et al., Immunology Today 4:72 (1983); (Cole et al., pg 77-96 in Monoclonal Antibodies and Cancer Therapy, Alan R. Liss, Inc. (1985). Monoclonal antibodies may be produced by hybridomas, which are immortalized cell lines capable of secreting a specific monoclonal antibody. The immortalized cell lines may be created in vitro by fusing two different cell types, usually lymphocytes, one of which is a tumor cell.

The anti-ADP antibodies may comprise antibodies from polyclonal sera (i.e., polyclonal antibodies). Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the ADP, derivative, a homologue or a variant as well as fragments or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate).

A composition according to the present invention may contain an oil-in-water (O/W), water-in-oil (W/O) or water-in-oil-in-water (W/O/W) type emulsion, which O/W/, W/O or W/O/W type emulsion serves as an adjuvant. In one aspect, the emulsion may be an O/W emulsion. An emulsion according to the disclosure may be prepared according to traditional; methods of preparation of an emulsion, in particular according to the processes described in Patent Applications EP-A-489,181 and EP-A-481,982.

An emulsion according to the present disclosure may contain by weight, from about 5 to about 95% of an oil phase for about 95 to about 5% of an aqueous phase, and from about 25 to about 75% of an oil phase and about 75 to about 25% of an aqueous phase. The emulsion should be stable for at least about 12 months when it is stored at a temperature of about 4° C.

The oil constituting the oil phase may be a mineral oil, a non-mineral oil or a mixture of a mineral oil and a non-mineral oil. The mineral oil may be natural or synthetic, and made from vegetable, animal or synthetic origin. All these oils lack toxic effects with respect to the host body to which the composition of the disclosure is administered. They may be liquid at the storage temperature (see above) or at least to make it possible to achieve liquid emulsions at said temperature. In embodiments, mineral oil according to the disclosure may consist of an oil comprising a linear carbon chain having a number of carbon atoms which is greater than 16, free from aromatic compounds. Such oils may be, for example, those marketed under the name MARCOL 52™ (produced by Esso France) or DRAKEOL 6VR™ (Produced by Penreco USA), which are both commercial mineral oils having a linear hydrocarbon chain, free of aromatic compounds.

By way of synthetic organic oils, polyisobutene, or polyisoporpenes may be used. Among vegetable oils, oleic acid-rich unsaturated oils which are biodegradable may be used, for example, those oils from groundnut, olive, sesame, soybean or wheat germ oils may be included.

The animal oils may include, but are not limited to, squalene or spermaceti oil.

In addition to the oil phase and aqueous phase, the composition may include an immune stimulating agent such as avridine. Moreover, the composition may contain a surfactant, where the latter displays a lipophilic or hydrophilic character characterized by an HLB (hydrophilic-lipophilic balance) value of between about 1 and about 19.

In embodiments, the surfactant may contain an ester obtained by condensing a fatty acid, which fatty acid is a liquid at 20° C., with a sugar or glycerol. Said sugar includes, but is not limited to, glucose, sucrose, or mannitol. In one aspect, the sugar is mannitol, and the ester is a mannitol ester. In one aspect, the mannito ester is an oleate obtained by anhydridizing the polyhydroxylated carbon atom of mannitol which is cyclized at positions 1-4 or 2-6.

Derivatives of these esters may also be employed. The derivatives display a hydrophilicity which is modified by grafting of hydrophilic functions such as alcohols, polyol, ethylene oxide, propylene oxide, carboxylic acid, amine or amide.

A surfactant of the instant disclosure may be pharmaceutically acceptable for use as an injectable preparation, it may lack heavy metals and possess very low acid or peroxide values. In embodiments, the surfactant is combined with the oil before formation of the emulsion. Oils combined with a surfactant are those marketed by SEPPIC (France), such as MONTANIDE (mixture of oil and surfactant), for example MONTANIDE ISA 25 and ISA 206.

In addition to the above, inulin containing adjuvants, including but not limited to, inulin acetate may be added to or be used to encapsulated vaccine-adjuvant compositions, where such inulin or inulin acetate (InAcT) may be prepared as recited in U.S. Pub. No. 20130195930, herein incorporated by reference in its entirety.

The immunization protocol may be selected by one skilled in the art without undue experimentation.

In another embodiment of the present invention, a method is provided for preparing a vaccine against RVFV. In one aspect, the method comprises providing an ADP, a derivative, a homologue or a variant or fragments thereof. Alternately, the method for preparing a vaccine against RVFV may include mixing the ADP polypeptide with a physiologically acceptable carrier or diluent. Generally, vaccines are prepared as injectables, in the form of aqueous solutions or suspensions. Vaccines in an oil base are also well known such as for inhaling. Solid forms which are dissolved or suspended prior to use may also be formulated. Pharmaceutical or physiological carriers are generally added that are compatible with the active ingredients and acceptable for pharmaceutical use. Examples of such carriers include, but are not limited to, water, saline solutions, dextrose, or glycerol. Combinations of carriers may also be used. One of ordinary skill in the art would be familiar with pharmaceutically or physiologically acceptable carriers or diluents.

In view of the above, the present disclosure also provides for a vaccine. In another embodiment, there is provided a vaccine which includes at least one ADP, a derivative, a homologue or a variant or fragment thereof. In another aspect, the vaccine comprises a nucleic acid encoding an ADP polypeptide, a derivative, a homologue or a variant or fragment thereof.

Useful vehicles are well known in the art, and include, e.g., water, buffered water, saline, glycine, hyaluronic acid and the like. The resulting aqueous solutions may be packaged for use as is, or lyophilized, the lyophilized preparation being rehydrated prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

Administration of the subunit vaccine as disclosed herein may be carried out by any suitable means, including both parenteral injection (such as intraperitoneal, subcutaneous, or intramuscular injection), and by topical application of the vaccine (typically carried in the pharmaceutical formulation) to an airway surface. Topical application of the vaccine to an airway surface can be carried out by intranasal administration (e.g. by use of dropper, swab, or inhaler which deposits a pharmaceutical formulation intranasally). Topical application of the vaccine to an airway surface can also be carried out by inhalation administration, such as by creating respirable particles of a pharmaceutical formulation (including both solid particles and liquid particles) containing the vaccine as an aerosol suspension, and then causing the subject to inhale the respirable polypeptides. Methods and apparatus for administering respirable polyopeptides of pharmaceutical formulations are well known, and any conventional technique can be employed. As a result of the vaccination the host becomes at least partially or completely immune to RVFV infection of the serotypes administered, or resistant to developing moderate or severe RVFV infection.

Viral subunits may be obtained from RVFV using biochemical methods or they may be expressed by recombinant means in suitable cells, for example, eukaryotic cells. Methods of expressing viral subunits are common in the art. For example, methods of expressing viral subunits are described in the following articles and in the references cited therein: Possee, 1986, Virus research 5:43; Kuroda et al. 1986, EMBO J. 5: 359; Doerfler, 1986, Curr. Topics Microbiol. Immunol. 131:51; Rigby, 1983, J. Gen. virol. 64:255; Mackett et al., 1985, In: DNA Cloning. A Practical Approach, Vol II, Ed., E. M. Glover, IRL Press, Washington, D.C.; Rothestein, 1985, In: DNA Cloning, A Practical Approach, Supra; Kinney et al., 1988, J. Gen. Virol. 69:3005; Panical et al., 1983, Proc. Natl. Acad. Sci. USA 80:5364; Small et al., 1985, In: Vaccinia Viruses as Vectors for Vaccine Antigens, pp. 175-178, Ed. J. Quinnan, Elsevier, N.Y.

In the practice of one embodiment of this invention, the N, Gn, Gc, Gn/Gc, NSs, or NSm subunits, or combinations thereof, may be produced in vitro by recombinant techniques in large quantities sufficient for use in a subunit vaccine.

In another aspect, the N, Gn, Gc, Gn/Gc, NSs, or NSm subunits, or combinations thereof, may be expressed by a recombinant vector, viral vector, or virus. In another aspect, the recombinant vector, viral vector, or virus expressing the subunit may itself serve as a vaccine component acting as a as an antigen or an adjuvant and eliciting or enhancing the subject's immune response to a N, Gn, Gc, Gn/Gc, NSs, or NSm subunit.

To make a recombinant virus vector that expresses the N, Gn, Gc, Gn/Gc, NSs, or NSm subunit antigen or immunogenic fragment thereof, a cDNA encoding the N, Gn, Gc, Gn/Gc, NSs, or NSm subunit antigen or immunogenic fragment thereof is inserted into the genome of a virus vector, for example, live adenovirus, poxvirus, baculvirus, pseudorabies virus (PRV), Venezuelan equine encephalitis (VEE) vectors such as strains V3526 or TC-83, and viral replicon particles (VRPs) derived from VEE, equine arteritis virus (EAV), or transmissible gastroenteritis virus (TGE). Recombinant viral vectors may be produced by any standard recombinant DNA techniques known to those skilled in the art (Ausubel et al., Current Protocols in Molecular Biology, Green Publishing Associates & Wiley Interscience, New York, 1989) for introduction of nucleotide changes into cloned DNA. A viral genome may then be ligated into an appropriate vector for transfection into host cells for the production of viral progeny.

In embodiments, the vaccine may contain isolated and purified N, Gn, Gc, Gn/Gc, NSs, or NSm subunit antigen or immunogenic fragment thereof. In one aspect, the N, Gn, Gc, Gn/Gc, NSs, or NSm subunit antigen or immunogenic fragment thereof is produced in a recombinant bacterium or eukaryote expression vector which produces the antigen which is isolated and purified to make the vaccine. For example, the N, Gn, Gc, Gn/Gc, NSs, or NSm subunits antigen or immunogenic fragment thereof is produced in a microorganism such as bacteria, yeast, or fungi; in a eukaryote cell such as a mammalian or an insect cell; or, in a recombinant virus vector such as adenovirus, poxvirus, herpesvirus, Simliki forest virus, baculovirus, bacteriophage, sindbis virus, sendai virus, live Venezuelan equine encephalitis (VEE) vectors such as strains V3526 or TC-83, and viral replicon particles (VRPs) derived from VEE, equine arteritis virus (EAV), or transmissible gastroenteritis virus (TGE). Suitable bacteria for producing the N, Gn, Gc, Gn/Gc, NSs, or NSm subunit antigen or immunogenic fragment thereof include *Escherichia coli, Bacillus subtilis*, or any other bacterium that is capable of expressing heterologous polypeptides. Suitable yeast types for expressing the N, Gn, Gc, Gn/Gc, NSs, NSm subunit antigen or immunogenic fragment thereof include *Saccharomyces cerevisiae, Schizosaccharomyces pombe, Candida*, or any other yeast capable of expressing heterologous polypeptides. Methods for using the aforementioned bacteria, recombinant virus vectors, eukaryote cells to produce antigens for vaccines are well known in the art.

To produce the vaccine consisting of the N, Gn, Gc, Gn/Gc, NSs, or NSm antigen or immunogenic fragment thereof, the nucleic acid encoding the N, Gn, Gc, Gn/Gc, NSs, or NSm antigen or immunogenic fragment thereof is in a plasmid and the nucleic acid is operably linked to a promoter which effects the expression of the N, Gn, Gc, Gn/Gc, NSs, or NSm antigen or immunogenic fragment thereof in a microorganism. Suitable promoters include, but are not limited to, T7 phage promoter, T3 phage promoter, beta-galactosidase promoter, and the Sp6 phage promoter. Expression of the N, Gn, Gc, Gn/Gc, NSs, or NSm antigen or immunogenic fragment thereof in a microorganism enables the N, Gn, Gc, Gn/Gc, NSs, or NSm antigen to be produced using fermentation technologies which are used commercially for producing large quantities of recombinant antigenic polypeptides. Methods for isolating and purifying antigens are well known in the art and include methods such as gel filtration, affinity chromatography, ion exchange chromatography, or centrifugation.

To facilitate isolation of the N, Gn, Gc, Gn/Gc, NSs, or NSm antigen or immunogenic fragment thereof, a fusion polypeptide may be made wherein the subunits are linked to linked to another polypeptide which enables isolation by affinity chromatography. In embodiments, a fusion polypeptide is made using one of the expression systems infra. For example, the cDNA nucleic acid sequence encoding the N, Gn, Gc, Gn/Gc, NSs, or NSm antigen or immunogenic fragment thereof is linked at either the 5' end or 3' end to a nucleic acid encoding a polypeptide. The nucleic acids are linked in the proper codon reading frame to enable production of a fusion polypeptide wherein the amino and/or carboxyl terminus of the N, Gn, Gc, Gn/Gc, NSs, or NSm or portion thereof is fused to a polypeptide which allows for the simplified recovery of the antigen as a fusion polypeptide.

An example of a prokaryote expression system for producing a N, Gn, Gc, Gn/Gc, NSs, or NSm subunit or immunogenic fragment thereof for use in vaccines is the Glutathione S-transferase (GST) Gene Fusion System available from Amersham Pharmacia biotech, Piscataway, N.J., which uses the pGEX-4T-1 expression vector plasmid. The cDNA encoding the N, Gn, Gc, Gn/Gc, NSs, or NSm subunit or immunogenic fragment thereof is fused in the proper codon reading frame with the DNA encoding GST. The GST part of the fusion polypeptide allows the rapid purification of the fusion polypeptide using glutathione Sepharose 4B affinity chromatography. After purification, the GST portion of the fusion polypeptide can be removed by cleavage with a site-specific protease such as thrombin or factor Xa to produce an antigenic determinant free of the GST polypeptide. The N, Gn, Gc, Gn/Gc, NSs, or NSm antigen or immunogenic fragment thereof free of the GST polypeptide is produced by a second round of glutathione Sepharose 4B affinity chromatography.

Another method for producing a vaccine comprising the N, Gn, Gc, Gn/Gc, NSs, or NSm antigen or immunogenic fragment thereof is a method which links in-frame with the cDNA encoding the antigenic determinant, DNA codons that encode polyhistidine. The polyhistidine typically comprises six histidine residues which allows purification of the fusion polypeptide by metal affinity chromatography, preferably nickel affinity chromatography. To produce the N, Gn, Gc, Gn/Gc, NSs, or NSm antigen or immunogenic fragment thereof free of the polyhistidine, a cleavage site such as an enterokinase cleavage site is fused in the proper reading frame between the codons encoding the polyhistidine and the codons encoding the antigen. The antigen free of the polyhistidine is made by removing the polyhistidine by cleavage with enterokinase. The antigen free of the polyhistidine is produced by a second round of metal affinity chromatography which binds the free polyhistidine. See Motin et al. Infect. Immun. 64: 4313-4318 (1996). The Xpress System, available from Invitrogen, Carlsbad, Calif., is an example of a commercial kit which is available for making and then isolating polyhistidine-polypeptide fusion protein.

Immunogenic compositions including vaccines may be prepared in a variety of formulations, for example, injectibles, liquid solutions or emulsions. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof.

Immunogenic compositions and vaccines may be administered parenterally, by injection subcutaneously or intramuscularly or in any other suitable manner. The immunogenic preparations and vaccines are administered in a manner compatible with the dosage formulation, and in such amount as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner. However, suitable dosage ranges are readily determinable by one skilled in the art and may be of the order of micrograms of the immunogens. Suitable regimes for initial administration and booster doses are also variable, but may include an initial administration followed by subsequent administrations. The dosage may also depend on the route of administration and will vary according to the size of the host.

The concentration of the immunogens in an immunogenic composition according to the invention is in general about 1 to about 95%. Immunogenicity can be significantly improved if the antigens are co-administered with adjuvants, commonly used as 0.005 to 0.5 percent solution in phosphate buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune response to, for example, vaccines. The vaccines of the present invention may be used in conjunction with an adjuvant, for example, lipopolysaccharides, aluminum hydroxide and aluminum phosphate (alum), saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. Desirable characteristics of ideal adjuvants include: (1) lack of toxicity; (2) ability to stimulate a long-lasting immune response; (3) simplicity of manufacture and stability in long-term storage; (4) ability to elicit both CMI and HIR to antigens administered by various routes; (5) synergy with other adjuvants; (6) capability of selectively interacting with populations of antigen presenting cells (APC); (7) ability to specifically elicit appropriate T-cell helper 1 (TH 1) or TH 2 cell-specific immune responses; and (8) ability to selectively increase appropriate antibody isotype levels (for example, IgA) against antigens. An adjuvant used with the present invention need not possess all these characteristics to be used with the present invention.

The route of administration for any one of the embodiments of the vaccine of the present invention includes, but is not limited to, oronasal, intramuscular, intraperitoneal, intradermal, subcutaneous, intravenous, intraarterial, intraocular, and oral as well as transdermal or by inhalation or suppository. The vaccine can be administered by any means which includes, but is not limited to, syringes, nebulizers, misters, needleless injection devices, or microprojectile bombardment gene guns (Biolistic bombardment).

The invention further relates to diagnostic and pharmaceutical kits comprising one or more containers filled with one or more of the ingredients of the aforementioned compositions of the invention, for example, nucleic acids encoding an ADP, and ADP, a derivative, a homologue or a variant or fragment thereof, or an antibody directed towards and ADP, a derivative, a homologue or a variant or a fragment thereof or a vaccine including an ADP or a nucleic acid encoding an ADP. Thus, the polynucleotides, polypeptides, and antibodies, and vaccines of the present disclosure may be employed as research reagents and materials for treatments of and diagnostics for RVFV. In particular, it is contemplated that the kits may be used to determine whether a subject was successfully vaccinated so that antibodies directed towards ADP are present in the collected sample. For example, a biological sample from an animal, e.g., a sheep, vaccinated with an ADP described above is collected and incubated with an ADP or other anti-ADP antibody preparation for a time sufficient for antibody binding to take place. The antibody binding to the ADP or other anti-ADP antibody preparation is detected using methods known to one of ordinary skill in the art, for example Western Blot analysis and/or ELISA assays.

Antibodies are disclosed herein may be monoclonal antibodies that may be whole immunoglobulins of any class e.g. IgG, IgM, IgA, IgD or IgE, chimeric antibodies or hybrid antibodies with specificity to two or more antigens of the disclosure. They may also be fragments e.g. F(ab')2, Fab', Fab, Fv and the like including hybrid fragments.

Methods of making monoclonal antibodies are well known in the art and can include the fusion of splenocytes with myeloma cells (Kohler and Milstein 1975 Nature 256; 495; Antibodies-a laboratory manual Harlow and Lane 1988). Alternatively, monoclonal Fv fragments can be obtained by screening a suitable phage display library (Vaughan T J et al 1998 Nature Biotechnology 16; 535). Monoclonal antibodies may be humanized or part humanized by known methods.

The anti-ADP antibodies of the invention have various utilities. For example, anti-ADP antibodies may be used in diagnostic assays for RVFV, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases (Zola, Monoclonal Antibodies: A Manual of Techniques, CRC Press, Inc. (1987) pp. 147-158). The antibodies used in the diagnostic assays can be labeled with a detectable moiety. Detection of an antibody to a detectable moiety. Examples of detectable moieties include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $I^{125}$, $I^{131}$, $S^{35}$ or $H^3$. The detectable moiety should be capable of producing, either directly or indirectly, a detectable signal. Any method known in the art for conjugating the antibody to the detectable moiety may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem. 30:407 (1982). The present inventors contemplate that such diagnostic kits would be of value in eradication programs for RVFV at multiple levels, including but not limited to an individual (farm), regional, and/or national level.

Anti-ADP antibodies also are useful for the affinity purification of ADP from recombinant cell culture or natural sources. In this process, the antibodies against ADP are immobilized on a suitable support, such a Sephadex resin or filter paper, using methods well known in the art. The immobilized antibody then is contacted with a sample containing the ADP to be purified, and thereafter the support is washed with a suitable solvent that will remove substantially all the material in the sample except the ADP, which is bound to the immobilized antibody. Finally, the support is washed with another suitable solvent that will release the ADP from the antibody.

While the invention has been described with reference to ADP, it is to be understood that this covers a derivative, a homologue or a variant or fragment thereof and similar proteins with additions, deletions or substitutions which co not substantially affect the protective antigenic properties of the recombinant protein.

The amount of vaccine sufficient to confer immunity to RVFV is determined by methods well known to those skilled in the art. This quantity will be determined based upon the characteristics of the vaccine recipient and the level of immunity required. Typically, the amount of vaccine or dosage to be administered will be determined based upon the judgment of a skilled veterinarian or can be readily determined by routine experimentation. The amount of virus vaccine of each strain may be adjusted, i.e. increased or decreased, to result in a formulation which provides sufficient protection from infection with the desired RVFV. As disclosed herein, different strains may be combined in any amount determined to be effective in preventing or treating RVFV infection of a strain in the vaccine formulation, and possibly other strains if crossprotection occurs. Cross-protection to infection by other RVFV strains may depend on the order in which RVFV strains are administered or whether the subject has been subjected to a prior RVFV infection as described above.

Host cells which can be used for the expression of chimeric proteins and the production of virus-like particles in accordance with the invention are in particular eukaryotic cells, and in particular insect cells, for example Spodoptera frugiperda cells.

Vectors which can be used in these insect cells are in particular vectors derived from baculoviruses. Methods for the cloning and expression of recombinant proteins in a baculovirus/insect cell system and vectors which can be used for carrying out these methods are known to persons skilled in the art, and are described for example in BACULOVIRUS EXPRESSION VECTORS: A LABORATORY MANUAL. Freeman and Cie, New York, (1992). Other methods and other vectors which can also be used are described, for example, in application EP 0 345 152, in application EP 0 651 815, or in application EP 0 638 647 in the names of INSTITUT NATIONAL DE LA RECHERCHE AGRONOMIQUE and of CENTRE NATIONAL DE LA RECHERCHE SCIENTIFIQUE and in PCT application WO 95/20672.

The following examples are intended to illustrate but not limit the invention.

EXAMPLES

Materials and Methods

Cloning and Construction of Recombinant Bacmid

The full-length coding sequences of the RVFV nucleoprotein (N) and the non-structural protein (NSs) were amplified by PCR using a proof reading DNA polymerase, Pfx50 (Life Technologies/Invitrogen, Carlsbad, Calif.) and primers (Table 1) designed from published sequences RVFV strain ZH548 (Accession No. DQ380151).

TABLE 1

Primers USed for the Amplification of RVFV Protein-Coding Regions

| Primer | Orientation | Sequence | Target |
|---|---|---|---|
| JAR979* | Forward | CACCATGGACAACTATCAAGACCTTGCGATCC (SEQ ID NO: 11) | N cds |
| JAR980* | Reverse | GGCTGCTGTCTTGTAAGCCTGAGCG (SEQ ID NO: 12) | Ncds |
| JAR981* | Forward | CACCATGGATTACTTTCCTGTGATATCTGTTGATTTG (SEQ ID NO: 13) | NSs cds |
| JAR982* | Reverse | ATCAACCTCAACAAATCCATCATCATCACTCTCC (SEQ ID NO: 14) | NSs cds |
| JAR975* | Forward | CACCATGATTGAAGGAGCTTGGGATTC (SEQ ID NO: 15) | NSm cds |
| JAR976* | Reverse | AGCAAAAACAACAGGTGCCAAAGC (SEQ ID NO: 16) | Nsm cds |
| JAR996$^a$* | Forward | CACCATGACAGTCCTTCCAGCCTTAG (SEQ ID NO: 17) | Gne or Gc cds |
| JAR111* | Reverse | GGCACTGAGAGCAGTGTGACACTG (SEQ ID NO: 18) | Gne cds |
| JAR987* | Reverse | TGAGGCCTTCTTAGTGGCAGCAAG (SEQ ID NO: 19) | GC cda |
| JAR990± | Forward | CCCAGTCACGACGTTGTAAAACG (SEQ ID NO: 20) | M113 Seq Primer |
| JAR991± | Reverse | AGCGGATAACAATTTCACACAGG (SEQ ID NO: 21) | M13 Seq Primer |

$^a$A signal peptide specific primer common for structural glycoproteins, Gne and Gc.
*Primers designed in house,
±Heidecker et al., Gene (1980) 10:69-73.
N, nucleoprotein;
cds, coding sequence;
NSs, non-structural protein S;
NSm, non-structural protein m;
Gne, octodomain of Gn glycoprotein,
Gc, Gc glycoprotein.

Plasmid pET30 Ek/LIC containing the entire coding region of the S segment of ZH548 was used as template for the PCR. The ectodomain and full-length coding sequences of the virus structural glycoproteins, Gn and Gc, as well as the non-structural protein, NSm, were synthesized according to the published sequences of ZH548 strain (Genewiz, San Diego, Calif.). Additionally for Gn, the cytoplasmic tail was deleted from the coding sequence. Amplicons were purified using Qiagen gel or PCR purification kit (Qiagen, Valencia, Calif.). The purified products were cloned into pFastBac/CT-TOPO vector (Life Technologies/Invitrogen, Carlsbad, Calif.). The TOPO cloning reactions were transformed into One Shot Mach1 T1 chemically competent E. coli to produce the respective donor plasmids, pRF-N, pRF-NSs, pRF-Gn, pRF-Gc and pRF-NSm. The sizes and sequences of the inserts in the donor plasmids were confirmed by PCR using gene-specific primers (Table 1), confirmed by restriction enzyme analysis and DNA sequencing Donor plasmids containing the gene of interest were purified from the E. coli transformants using Qiagen Miniprep kit (Qiagen, Valencia, Calif.). The constructs were transformed into MAX Efficiency DH10Bac competent E. coli to generate recombinant bacmid by site-specific transpositioning. Recombinant bacmids were purified suing HiPure Plasmid Miniprep kit. Transpositioning of the gene of interest into a recombinant bacmid was confirmed by PCR using M13F and M13R primers (Heidecker, et al. 1980).

Signal Peptide Prediction and Modification of Gn and Gc

The RVFV M segment, which encodes the envelope glycoproteins, Gn and Gc, has at least four translation initiation sites within the single mRNA transcribed from the M segment. We hypothesized that sequences starting from one of the initiation codons (ATG) to the start of Gn may serve as a signal peptide and guide the translocation of the polyprotein from the cytoplasm to the endoplasmic reticulum (ER). Prediction of signal peptides and signal peptidase cleavage sites were performed using hidden Markov model and neural network model prediction programs at SignalP 3.0. A 54-nucleotide sequence (SEQ ID NO:1) beginning from the fifth ATG or the RVFV M segment, upstream of Gn coding sequence, was identified as a strong signal peptide with a single signal peptidase cleavage site. To ensure expression of glycosylated forms of the proteins, this signal sequence was fused to the N-terminus of Gn and Gc and amplified by PCR using primers shown in Table 1. The sequences were cloned into recombinant bacmids and expressed in a baculovirus expression system (LifeTechnologies/Invitrogen, Carlsbad, Calif.).

Expression and Purification of Recombinant RVFV Proteins

To express recombinant RVFV proteins, highly purified recombinant bacmids were transfected, using Cellfectin II reagent (Life Technologies/Invitrogen Carlsbad, Calif.), into Spodoptera frugiperda, Sf9, cells (Life Technologies/Invitrogen) grown in Sf-900 II SFM medium (Life Technologies/Invitrogen, Carlsbad, Calif.) supplemented with 10% fetal bovine serum and 100 U/ml-100 pg/ml penicillin-streptomycin. Protein expression was carried out using P2 or higher passage recombinant baculovirus stock (>$10^7$ pfu/ml) in T75 or T175 Biolite flasks (ThermoFisher Scientific, Dubuque, Iowa). To visualize expression of recombinant proteins, samples were subjected to western blot analysis by resolving on 12% Bis-Tris polyacrylamid gel and detected using anti-His-HRP antibody. The proteins were expressed with a C-terminal 6xHis-tag and purification of recombinant proteins was carried out using Ni-NTA superflow resin (Novagen, Rockland, Md.) according to manufacturer's instructions. Recombinant proteins were eluted with an elution buffer containing 300 mM NaCl, 50 mM $Na_2PO_3$ (pH 8.0) and 250 mM imidazole and dialyzed overnight against storage buffer, PBS (pH 7.4) and 5% glycerol. The purified proteins were stained with coomassie blue and protein concentrations were determined using the bicinchoninic acid (BCA) assay (Thermo Scientific, Rockford, Ill.) with an absorbance of 562 nm, using bovine serum albumin (Sigma-Aldrich, St. Louis, Mo.) as protein standard. Aliquots were stored at −80° C. until used.

Immunofluorescence Antibody Assay

To confirm expression of recombinant RVFV proteins, immunofluorescence antibody assay was carried. Briefly, Sf9 cells were infected with recombinant baculovirus carrying RVFV N or Gn coding sequences. About 36 hrs later, cells were harvested and adhered to glass slides using a cytocentrifuge, Cytopro (Wescor, Logan, Utah) according to manufacturer's instruction and fixed in acetone for 5 min at −20° C. Slides were blocked in PBS containing 1% BSA at 37° C. for 45 min and then incubated for 30 min at 37° C. with mouse monoclonal antibodies, ID8 and 4D4 (provided by Dr. Connie W. Schmaljohn, the United States Army Medical Research Institute for Infections Diseases, USAMRIID), against N and Gn proteins, respectively. Slides were rinsed for 10 min in 1× fluorescence antibody (FA) rinse buffer (2.85 g $Na_2CO_3$, 8.4 g $NaHCO_3$, 2.125 g NaCl, distilled water to 1000 ml; pH 9 to 9.5) and the probed with anti-mouse FITC-conjugated secondary antibody for 30 min at 37° C. (Sigma-Aldrich, St. Louis, Mo. USA). Slides were rinsed for 10 min in 1×FA rinse buffer and counterstained with DAPI (Invitrogen, Molecular Probes) containing mounting medium. Slides were examined under a fluorescent microscope (Nikon, Eclipse 90i®) at 100× magnification.

Tunicamycin Assay

A baculovirus expression system was sued to produce glycosylated recombinant proteins, a posttranslational modification shown to enhance antigenicity/immunogenicity (Gavrilov et al., 2011). To confirm that the modified Gn and Gc proteins were glycosylated, a tunicamycin glycosylation inhibition assay was performed. For this, six well plates were seeded with $2 \times 10^6$ Sf9 cells per well and infected with recombinant baculoviruses expressing RVFV Gn or GC glycoproteins at MOI of 1. Immediately following infection, tunicamycin was added to each well at varying concentrations of 0.5 µg/ml, 1 µg/ml, 3 µg/ml, 6 µg/ml, 8 µg/ml and 10 µg/ml. Cells were harvested 5 days post infection (pi) and resuspended in PBS pH 7.4 containing 1× Complete protease inhibitor (Roche Diagnostics®, Indianapolis, Ind.). The samples were separated by SDS-PAGE in NuPAGE 12% Bis-Tris gels (Life Technologies/Invitrogen) and transferred onto polyvinylidene difluoride (PVDF) membranes (GE Healthcare, Amersham Hybond-P). The membranes were probed as described above using anti-His (C-terminal)-HRP monoclonal antibody (Life Technologies/Invitrogen, Carlsbad, Calif.). Reactivity was detected using AEC (3-Amino-9-ethyl-carbazole) peroxidase substrate system (Abcam, Cambridge, Mass.).

Rift Valley Fever Virus Anti-Sera

Sheep (Rambouillet) were vaccinated subcutaneously with $10^6$ pfu of RVFV-vaccine strain, MP12. These studies were performed at Kansas State University (Biosecurity Research Institute (BRI) BSL-3Ag facility) or the Arthropod-Borne Animal Diseases Research Unit (ABADRU) large animal isolation building (LAIB) in Laramie, Wyo. (day 28 sheep sera, P1-P6). Blood samples were collected from individual animals at specific time points (days) post vaccination (pv) for sera. Prevaccination blood samples were collected from each individual sheep prior to vaccination, which was used as pre-immune control sera. Day-28 post-infection (pi) antisera were obtained from previous sheep challenged at the CFIA BSL-3Ag facility in Winnipeg, Canada, with the wild-type RVFV ZH501 strain (sheep P7-P10). All sera were stored at −80° C. and heat-activated (56° C. for 30 min) prior to removal from the BSL-3Ag laboratory. Institutional Animal Care and Use Committee (IACUC) protocols were approved at Kansas State University (BRI) and University of Wyoming (ABADRU-LAB).

Western Blot Analysis

Briefly, approximately 5 pg of each of recombinant RVFV proteins was subjected to electrophoresis in 12% Bis-Tris polyacrylamide gel in 1×MOPS running buffer (Life Technologies/Invitrogen). The proteins were transferred by electroblotting onto PVDF membranes according to standard protocols. the membrane was blocked in 0.1% Tween-20 in PBS (pH 7.4) containing 3% bovine serum albumin (BSA) at room temperature for 1 hr. The blot was washed 3 times for 5 min each in 0.1% Tween-20 in PBS. All subsequent washing steps were carried out as described above. For analysis of recombinant protein expression, the membrane was incubated with anti-His-(C-Terminal)-HRP (Life Technologies/Invitrogen) diluted 1:5,000 in blocking solution. Expression of recombinant proteins, N and Gn, were further confirmed suing a primary antibody, mouse anti-N (R3-ID8) and mouse anti-Gn monoclonal antibody (4D4), respectively at a dilution of 1:2,000. For analysis of reactivity against sheep sera, the membrane was incubated with 1:100 dilution of each test serum for 1 hr at room temperature. After washing, the membrane was incubated for 1 hr at room temperature with Protein G-HRP (Abcam, Cambridge, Mass.) diluted 1:25,000. After the final washing steps, specific reactivity was detected using AEC (3-Amino-9-ethyl-carbazole)peroxidase substrate (Sigma-Aldrich, St. Louis, Mo.).

Indirect Enzyme-Linked Immunosorbent Assay (ELISA)

A 96-well plate (Nunc, Maxisorp®) was used for the indirect ELISA. Each well was coated overnight at 4° C. with 100 ng of recombinant protein in 100 ul of Dulbecco's coating buffer, pH 7.4 (Life Technologies/Invitrogen). Plates were blocked for 15 min at 37° C. with PBS (pH 7.4) containing 0.1% Tween and 1% skim milk. After washing three times with 0.1% Tween-20 in PBS, a volume of 200 μl of test serum, diluted 1:200 in the blocking solution, was added and incubated at 37° C. for 1 hr. All subsequent washing steps were carried out three times as indicated above. Each serum sample was tested in duplicate. Each test included a positive control, obtained from sheep challenged with a virulent strain of RVFV (ZH501), and negative controls obtained from the respective sheep prior to vaccination. After washing, plates were incubated with Protein G-HRP (Abcam, Cambridge, Mass.), diluted 1:50,000 in blocking solution, at 37° C. for 1 hr. Protein G has high binding affinity to IgG from sheep, goats, horses and rabbits, with little or no binding affinity to IgM. After washing, 100 pl of substrate buffer containing 0.1 mg/ml 3,3',5,5'-tetramethyl-benzadine (TMB) (Thermo Scientific, Rockford, Ill.) and $H_2O_2$ was added and plates were incubated in the dark for 25 min. The reaction was stopped with 2M $H_2SO_2$ and optical densities (OD) were measured at 450 nm. For each ELISA, the cut-off OD value was determined by addition of 2 standard deviations to the mean OD value of serum obtained from prevaccinated/non-infected sheep.

Cell Cultures

The African green monkey cells, Vero E6 (ATCC, Manassas, Va.), were maintained in Eagle's minimal essential medium (Corning Cellgro, Manassas, Va.) supplemented with 10% fetal bovine serum, L-glutamine and penicillin-streptomycin (Invitrogen-Life Technologies, Carlsbad, Calif.). The cultures were maintained at 37° C. in humidified 5% $CO_2$ atmosphere. The *Spodoptera frugiperda* (Sf9) cells (Invitrogen/Life Technologies) were maintained in SFM 900 II medium supplemented with 10% fetal bovine serum and penicillin-streptomycin (Invitrogen/Life Technologies). These cells were maintained at 27° C.

Detection of Recombinant Protein Expression and Analysis of Immunoreactivity

Approximately 5 μg of each purified recombinant protein was subjected to electrophoresis in 12% Bis-Tris polyacrylamide gel in 1×MOPS running buffer (Invitrogen-Life Technologies). The proteins were transferred onto PVDF membranes according to standard protocols. The membrane was blocked in blocking solution containing 0.1% Tween-20 in PBS (pH 7.4) and 3% bovine serum albumin (BSA) for 1 hr at room temperature or overnight at 4° C. Thereafter, the membrane was washed 3 times for 5 min each in 0.1% Tween-20 in PBS and then incubated with anti-His-(C-Terminal)-HRP (Invitrogen-Life Technologies) diluted 1:5,000 in blocking solution. Expression of recombinant proteins, N and Gne, were further confirmed using a primary antibody, mouse anti-N (R3-ID8) and mouse anti-Gn monoclonal antibody, 4D4, (a gift from Dr. Connie Schmaljohn, United States Army Medical Research Institute for Infectious Diseases), respectively at a dilution of 1:2,000. To probe immunoreactivity of antisera obtained from sheep vaccinated with recombinant RVFV Gn and Gc glycoprotein subunit vaccine or RVFV MP12 infected control sera, the blots were incubated with individual sheep sera at 1:100 dilution for 1 hr at room temperature. After washing, the membrane was incubated for 1 hr at room temperature with Protein G-HRP (Abcam, Cambridge, Mass.) diluted 1:25,000. After the final washing steps, specific reactivity was detected using AEC (3-Amino-9-ethyl-carbazole)peroxidase substrate (Sigma-Aldrich, St. Louis, Mo.) or ECL enhanced chemiluminescent detection system.

Preparation of the Vaccine and Animal Immunization

The purified glycoproteins were formulated in montanide ISA25 water-in-oil adjuvant (Seppic, France) to obtain a concentration of 50 μg of each immunogen per vaccine dose according to the manufacturer's instruction. Six sheep (#9, #36, #163, #169, #170, #179) were each immunized subcutaneously with a primary does of 50 μg of purified Gn and 50 μg of purified Gc. At day 21 post-primary vaccination, hereafter referred to simply as postvaccination (pv), each sheep was given a booster with the same amount of vaccine (a second dose). Blood samples were collected from the jugular vein from each sheep for the separation of sera prior to vaccination (day 0), in order to establish baseline prevaccination immune response status. Thereafter, serum samples were collected from each sheep weekly on days 7, 14, 21, 28, 35, 42 and 49 pv. All sera were stored at −80° C. until used. Animal experiments had the approval of the institutional Animal Care and Use Committee (IACUC) of South Dakota State University.

Immunogen-Specific Antibody Response

Specific antibody response in serum was measured by enzyme-linked immunosorbent assay (ELISA) using nickel column-purified baculovirus-expressed RVFV Gn, Gc and *E. coli*-expressed RVFV N proteins. The N protein was expressed in *E. coli*, using an expression construct kindly provided by Friedeman Weber, University of Marburg Germany, and was used as a negative diagnostic marker antigen to assess the DIVA compatibility of the recombinant subunit vaccine. To perform an ELISA, each well, in a 96-well plate (Nunc, Maxisorp®) format, was coated overnight at 4° C.

with approximately 100 ng of each purified recombinant protein in 100 μl of Dulbecco's coating buffer (pH 7.4) (Invitrogen-Life Technologies). Plates were blocked for 15 min at 37° C. with PBS (pH 7.4) containing 0.1% Tween and 1% skim milk. After washing three times with 0.1% Tween-20 in PBS, a volume of 200 μl of test serum, diluted 1:200 in the blocking solution, was added and incubated at 37° C. for 1 hr. All subsequent washing steps were carried out three times as indicated above. Each serum sample was tested in duplicate. Positive and negative control sera were included in each assay. Plates were incubated with Protein G-HRP (Abcam, Cambridge, Mass.), diluted 1:50,000 in blocking solution at 37° C. for 1 hr, washed, and a 100-ul aliquot of TMB Peroxidase Substrate and Peroxidase solution B (Thermo Scientific, Rockford, Ill.) and $H_2O_2$ was added to each well. Plates were held in the dark for 15-20 min. Color development was stopped by the addition of 2M $H_2SO_4$ to each well; and optical density (OD) at 450 nm was measured by using a microplate reader (FluoStar Omega, BMG LABTECH Inc., Cary, N.C.). The cut-off point in each ELISA was determined by the addition of two standard deviations to the corresponding mean OD value of the pre-vaccination serum. Mean OD values equal to or greater than the cut-off value were considered positive.

Anti-RVF Virus PRNT80

The stock of MP12 RVFV was diluted to 50 PFU in 205 μl of 1×MEM containing 4% bovine serum albumin (Sigma-Aldrich, St. Louis, Mo.). Separately, aliquots of serum from each vaccinated sheep were diluted as follows: 1:10, 1:20, 1:40, 1:80, 1:160, 1:320, 1:640, and 1:1280 in 1×MEM containing 2% bovine serum albumin and 1% penicillin streptomycin. Diluted serum (250 μl) was mixed with an equal volume of diluted MP12 virus and incubated at 37° C. for 1 hr. Thereafter, each mixture of serum plus RVFV was used to infect confluent monolayers of Vero E6 cells in 12-well plates. After 1 hr adsorption at 37° C. and 5% $CO_2$, the mixture was removed, and a 1.5 ml of nutrient agarose overlay (1×MEM, 4% bovine serum albumin, 0.9% Sea-Plaque agar) was added to the monolayers. After 5 days incubation, the cells were fixed with 10% neutral buffered formalin for 3 hrs prior to removal of the agarose overlay. The monolayer was stained with 0.5% crystal violet in PBS, and plaques were enumerated. the calculated PRNT80 corresponded to the reciprocal titer of the highest serum dilution, resulting in an 80% reduction in the number of plaques relative to the virus control.

Electron Microscopy

To examine or rule out possible assembly of recombinant Gn and Gc into VLPs upon mixing of the proteins into vaccine formulation, a transmission electron microscopy (TEM) was performed. Briefly, equal amounts of purified Gn and Gc were mixed together in a single tube and incubated for 30 min at room temperature. Alongside, aliquots of purified Gn and Gc were also made in separate tubes and incubated for 30 min as described above as controls. Subsequently, the proteins were nebulized on copper Formar-carbon coated grids (Tedd Pella Inc., Redding, Calif.), dried at room temperature for 30 min and stained with phosphotungstic acid (PTA). Images were recorded at a calibrated magnification of 30,000× or 60,000× using an electron microscope (FEI Technai G2 Spirit biot, Hillsboro, Oreg.).

Statistical Analysis

Data were analyzed using t-test of independent samples with equal or unequal variances. To reduce the effect of variable individual host immune response on reactivity, we calculated geometric means of OD values and analyzed the differences for statistical significance. To determine the significance of observed differences in the optical density (OD) values of prevaccination and postvaccination sera, a serum reactivity index (SRI) for each sheep, defined as the ratio of postvaccination serum OD value to the prevaccination serum OD value, was determined.

Example 1. Expression of RVFV Recombinant Proteins

Figure 2:
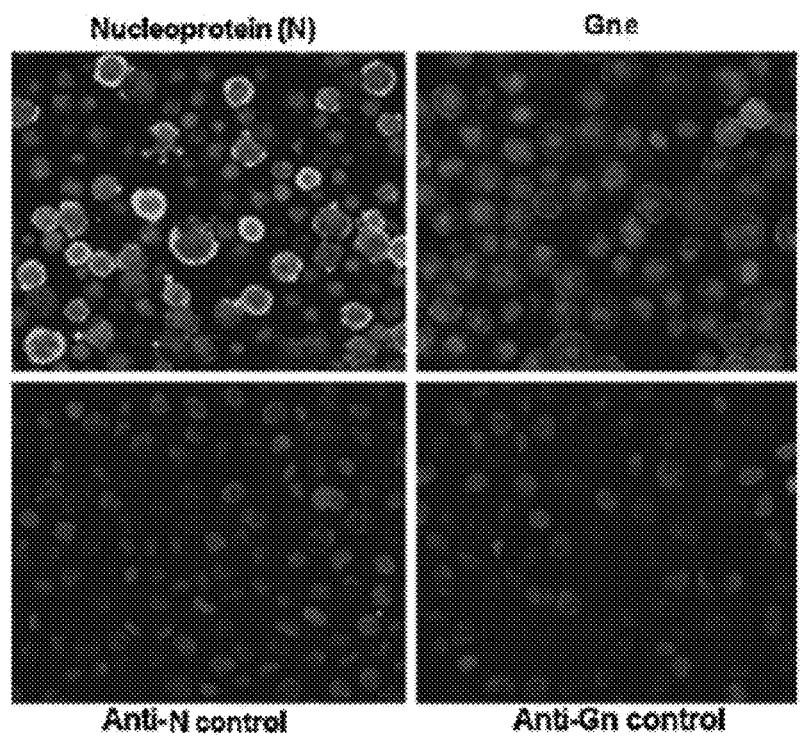
FIG. 2 shows the results of immunofluorescence antibody assays confirming expression of the recombinant proteins Gn and N in Sf9 cells. Monoclonal antibodies 4D4 and ID8 were used to detect expression of Gn and N, respectively. A specific green fluorescent signal around the nucleus of Gn-expressing cells is seen indicating that the recombinant protein is secreted within the cell. Control (Gn)=non-infected Sf9 cells stained with Gn monoclonal antibody (4D4) shows negative staining or anti-N control=non-infected Sf9 cells stained with N monoclonal antibody (ID8). The cell nucleus is stained in blue color.

Using recombinant baculovirus, RVFV structural (Gc, Gn and N) and non-structural proteins (NSs and NSm), each containing a hexahistidine tag at their C-terminus were expressed in a eukaryotic expression system using Sf9 cells. To ensure translocation in the ER and glycosylation of the structural glycoproteins, Gn and Gc, a signal peptide was fused upstream of the N-terminus of both proteins. Infection of Sf9 cells with recombinant baculovirus carrying the full-length Gn coding sequence resulted in no or low amount of Gn protein. In order to minimize interactions of the full length Gn with cellular membranes, only the ectodomain of the Gn protein without the transmembrane and cytosolic regions, was expressed. The proteins were detected by western blot using anti-His-HRP monoclonal antibody (FIG. 1a). Recombinant proteins of the expected molecular weights were expressed (Gc=60 kDa, Gn=54 kDa, N=30 kDa, NSs=33 kDa, NSm=17 kDa). Expression of N and Gn proteins was further confirmed by immunoreaction with anti-N and anti-Gn mouse monoclonal antibodies (FIG. 1b). Coomassie stained gels of the purified proteins are shown in FIG. 1c. Immunofluorescent antibody assay using the mouse monoclonal antibodies against the Gn and N proteins further confirmed the expression of the proteins in Sf9 cells (FIG. 2). A specific green immunofluorescent signal was observed on the surface, around the periphery of the cells expressing recombinant Gn, whereas both cytoplasmic and surface staining was seen with N (FIG. 2).

Figure 3:
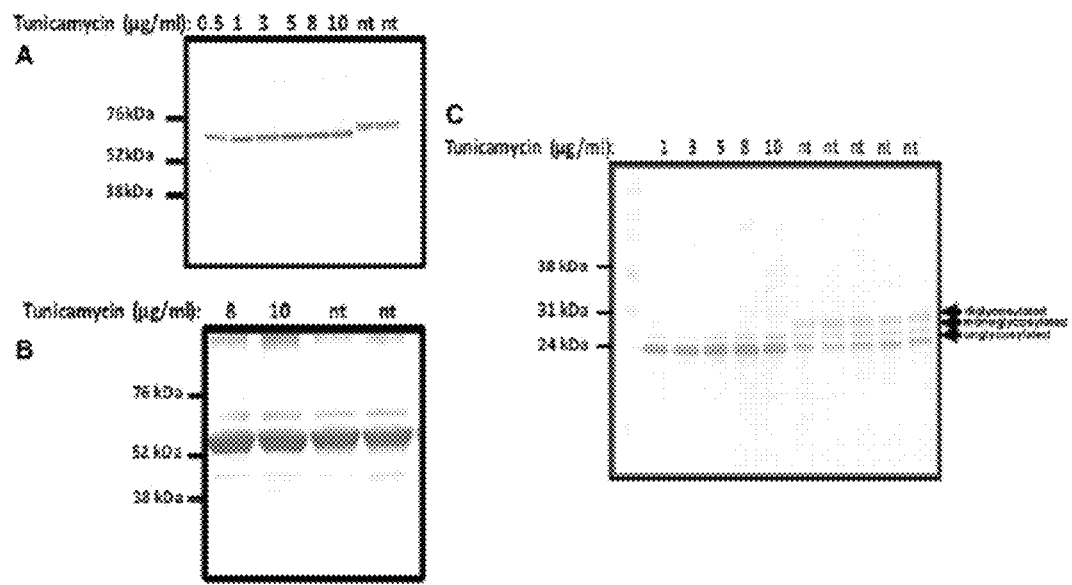
FIG. 3 shows the results of in vitro glycosylation assay of Rift Valley fever glycoproteins, Gc and Gn. (A) Treatment of Gc-recombinant baculovirus infected Sf9 cells with varying concentrations of tunicamycin (0.5 pg/ml-10 pg/ml) resulted in inhibition of glycosylation shown by a shift in electrophoretic migration. (B) Similar treatment of Gn (8 pg/ml and 10 pg/ml) resulted in marginal molecular weight shift (compare with non-treated, nt), since the protein has one putative N-glycosylation site; Gc has 4 putative N-glycosylation sites. Treatment of baculovirus expressed sheep prior protein (PrP) with varying concentrations of tunicamycin (1 µg/ml-10 pg/ml) resulted in inhibition of glycosylation of the protein(C). nt=non-treated controls; m=molecular weight marker.

Example 2. Determination of Protein Glycosylation State of Baculovirus Expressed Proteins It is known that the RVFV Gn and Gc glycoproteins carry one and four putative N glycosylation sites, respectively (Gerrard and Nichol 2007). In order to characterize glycosylation patterns of Gn and Gc, biochemical inhibition of N-glycosylation by treatment of cells with tunicamycin, a potent inhibitor of bacterial and eukaryote N-acetylglucosamine transferases, was carried out. Treatment of Sf9 cells infected with either recombinant Gc or Gn-baculoviruses with varying concentrations of tunicamycin (0.5 pg-10 pg) resulted in inhibition of glycosylation of the proteins demonstrated by a lower molecular weight of the reactive proteins when compared to non-treated controls. The shift was more obvious for Gc (FIG. 3a), known to have four putative glycosylation sites when compared to Gn (showing marginal shift), known to have only one glycosylation site (FIG. 3b). As a control, baculovirus-expressed sheep prion protein (PrP) expressed in Sf9 cells was used. Treatment with tunicamycin resulted in significant inhibition of N-glycosylation (FIG. 3c).

Example 3. Antibody Reactivity Against Recombinant Proteins

Figure 4:
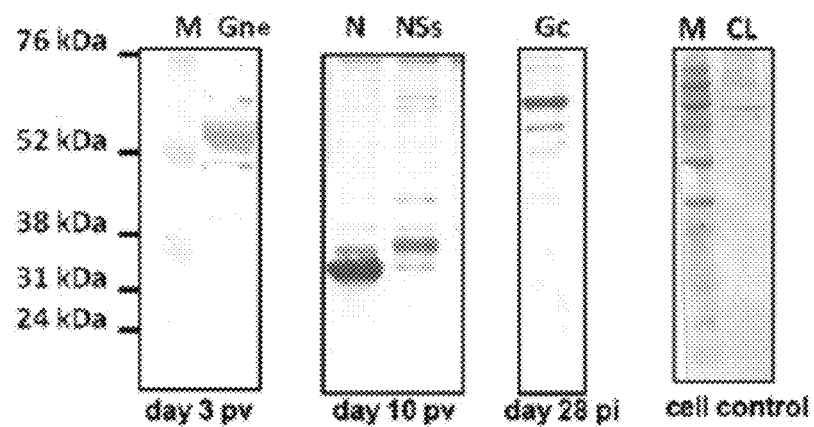
FIG. 4 shows a western blot demonstrating immunoreactivity of purified baculovirus expressed proteins with RVFV antisera from sheep. Reactivity shows that the proteins were expressed in the correct conformation. Gn=N-terminus glycoprotein; N=nucleoprotein; NSs=non-structural protein S segment; Gc=C-terminus glycoprotein; CL=non-infected cell lysate; m=molecular weight marker; pv=post vaccination; pi=post-infection.

Antibody reactivity against the recombinant proteins N, NSs, NSm, Gn and Gc was examined suing sera collected at different time points post-vaccination (pv) (days 3, 10 and 28) from MP12 vaccinated sheep. Recombinant N was reactive with day 3 pv sera and both N and NSs proteins showed antibody reactivity with day 10 pv and day 28 pv sera, with N showing consistently stronger reactivity than NSs (FIG. 4). Reactivity of the structural glycoproteins Gn and Gc showed that Gn was reactive with 1 or 2 serum samples on day 3 pv. Thereafter, it remained consistently reactive with all sera obtained on day 10 and 28 pv (Table 2).

TABLE 2

Reactivity of baculovirus-expressed Rift Valley fever virus proteins with sheep antisera determined by Western blot.

| Recombinant Proteins | MP12 vaccinated sheep sera: days pv | | | Wild type (ZH501) challenged sheep sera: 28 pi (Nsp/total sample tested) |
|---|---|---|---|---|
| | day 3 | day 10 | day 28 | |
| | (nsp/total sample tested) | | | |
| Gne | 1/2 | 4/4 | 10/10 | 4/4 |
| Gc | 0/2 | 1/4 | 9/10 | 4/4 |
| N | 2/2 | 4/4 | 10/10 | 4/4 |
| NSs | 0/2 | 4/4 | 9/10 | 4/4 |
| NSm | 0/2 | 0/4 | 0/10 | 0/4 | pv = post vaccination;
pi = post infection;
nsp = number of samples tested positive;
Gne = ectodomain of Gn glycoprotein;
Gc = Gc glycoprotein;
N = nucleoprotein;
NSs = non-structural protein S;
NSm = non-structural protein m The GC protein showed no reactivity at day 3 pv and weak reactivity with day 10 pv sera, where only 1 or the 4 serum samples tested was positive; it was 90% reactive with day 28 pv sera. To further examine reactivity of RVFV proteins, we performed immunoblot analysis using day 28 pi sera obtained from sheep infected with the wild type strain ZH501 of RVFV. Recombinant N and Gn proteins showed consistent and strong reactivity against all sera (4/4), NSs and Gc were also reactive against all sera (4/4) but with relative lower signal intensities. We did not detect specific reactivity with the NSm protein either with the MP12 vaccinated or ZH501 infected sheep sera.

Figure 5:
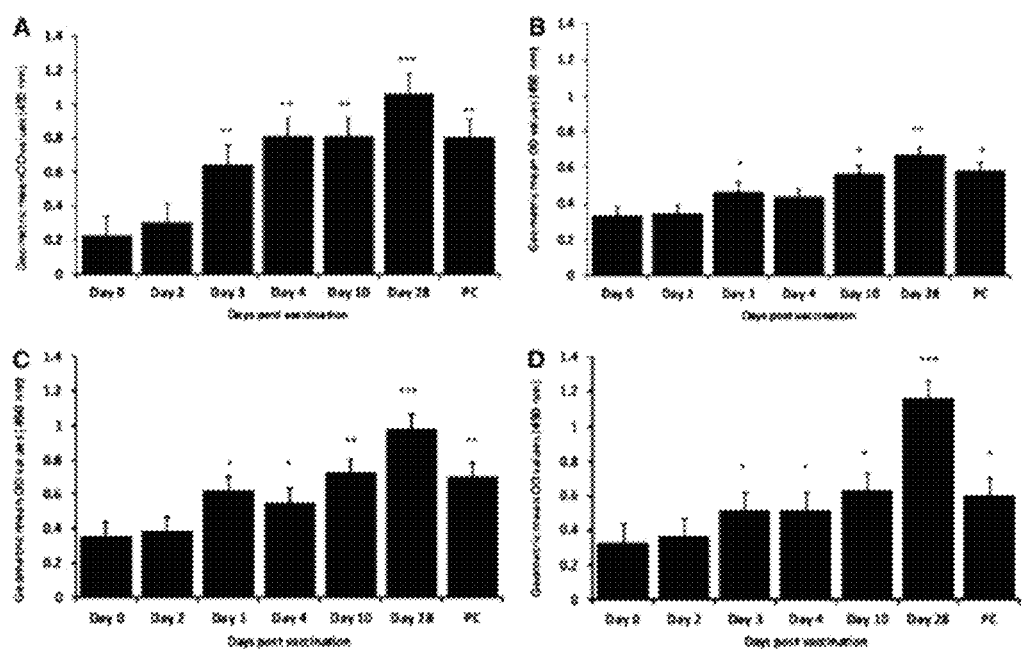
FIG. 5 shows the reactivity of recombinant RVFV proteins, nucleoprotein, N (A) non-structural protein, NSs (B), glycoprotein, Gn (C), glycoprotein, Gc (D) and non-structural protein NSm (E) with antisera from MP12 vaccinated sheep. Day 0 is pre-vaccination sera; PC=positive control sera derived from sheep challenged with RVFV wild type, ZH501; P1-P6 are day 28 sera from sheep vaccinated with MP12 RVFV strain (Laramie, Wyo.); P7-P10 are day 28 sera from sheep infected with the wild type virus (ZH501). Asterisks (*) denote level of statistical significance and show that differences in OD values of sera tested for each of the time-points was significantly different (P<0.05) from day 0 (pre-vaccination) sera. Cut-off OD value for each ELISA was determined by addition of 2 standard deviations to the mean OD value of serum obtained from prevaccinated/non-infected sheep (N=0.320; NSs=0.358; Gn=0.395; Gc=0.387; NSm=0.028.

Example 4. Antibody Reactivity of Recombinant Protein Against Sheep Sera Vaccinated with RVFV An indirect ELISA was developed to assess antibody reactivity of the recombinant proteins against sera obtained from sheep vaccinated with RVFV MP12 vaccine strain or challenged with wild type ZH501 RVFV strain. For MP12 vaccinated sheep sera, the recombinant proteins, N, NSs, NSm, Gc, and Gn showed time-dependent increase in reactivity, shown by an increase in OD values (FIGS. 5a-e). A consistent strong reactivity for all proteins was observed with day 28 sera. There was particularly strong antibody reactivity with N and to a lesser extent with Gn on day 3 pv (FIGS. 5a and 5c). The level of reactivity with NSs was also strong but had comparatively lower OD values (FIG. 5b). Reactivity with Gc was high on day 10 pv and was strongest on day 28 (FIG. 5d). For the wild type exposure-derived sheep sera, the recombinant proteins. N, NSs, Gn and Gc were reactive with the day 28 pi. In contrast, NSm showed low reactivity manifested by relatively low OD values with sera from both MP12 and wild type infected sheep (FIG. 5e). Sera from three sheep (infected with the wild-type ZH501, P7 and P10, and MP-12 immunized sheep, P5) showed significant reactivity (P<0.05) in comparison with the negative control (day 0 serum). The positive sera were obtained from sheep on day 28 pi with the wild type Rift Valley fever virus, ZH501.

Example 5. Immunogenicity of Gn and Gc Glycoproteins

Figure 6:
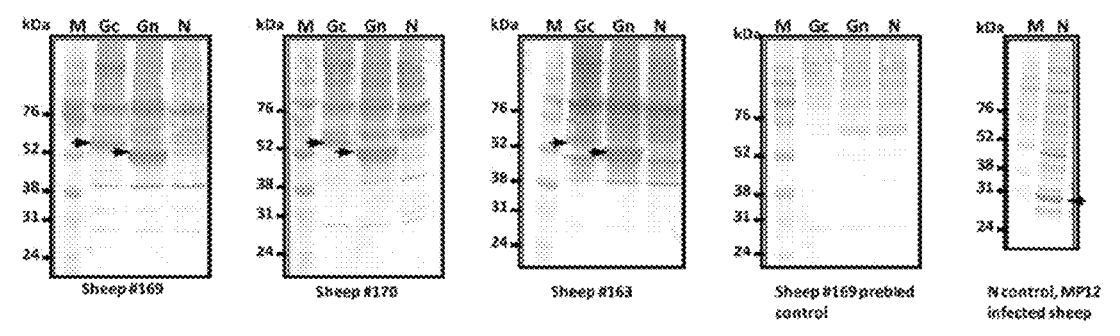

To examine vaccine-induced immunoreactivity, day 28 pv antisera from sheep #169, #170 and #163 were examined by immunoblot analysis. Antisera from all three sheep showed specific reactivity with the vaccine antigens, Gn and Gc (FIG. 6) but not with the control N protein. Day 0 serum, obtained prior to vaccination, did not show specific reactivity with any of the proteins. As a positive control, a day 28 MP12 post-infection sheep serum showed specific reactivity with the baculovirus-expressed N protein confirming the specificity of the recombinant proteins (FIG. 6).

Figure 7:
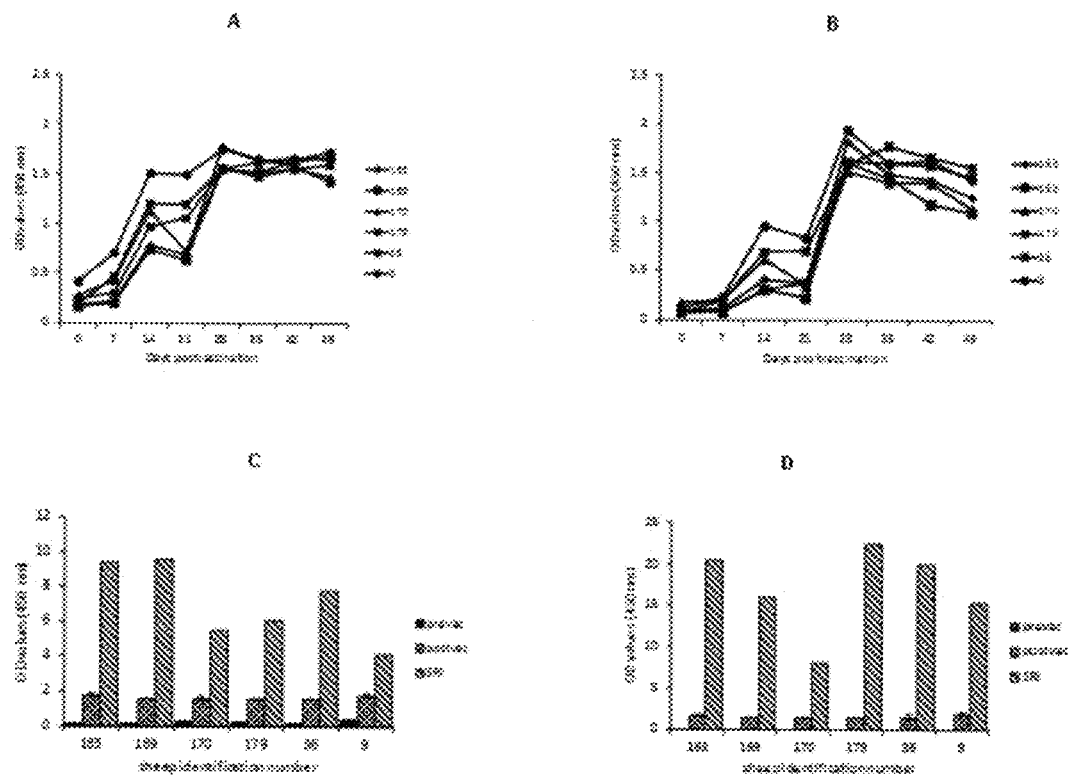
FIG. 7 shows the analysis of vaccine-induced IgG host antibody response by antigen-specific indirect ELISAs, Gn-ELISA (A) and Gc-ELISA (B) depict time-dependent increase in specific antibody titer. Analysis of serum reactivity indices (SRI) using prebled sera against day 28 pv sera show significant increase in specific antibody titers (P<0.05) demonstrated by high SRI values in both Gn-ELISA (C) and Gc-ELISA (D). Prevac=prevaccination serum; postvac=postvaccination serum; SRI=serum reactivity index. The cut-off value for individual sheep in Gn-ELISA: #163=0.354; #169=0.167; #170=0.507; #179=0.365; #36=0.252; #9=0.668. The cut-off value in Gc-ELISA: #163=0.215; #169=0.151; #170=0.309; #179=0.104; #36=0.7135; #9=0.259. A cut-off value was determined for each sheep as described in materials and methods.

To examine vaccine-induced seroconversion and the kinetics of antibody response, sera collected from the vaccinated sheep at various time points pv(day 0, 7, 14, 21, 28, 35, 42, and 49). were tested in Gn and Gc-specific indirect ELISAs. Antibody reactivity with Gn antigen was detected in three of the sheep at day 7 pv (FIG. 7a). At day 14 pv, all sheep seroconverted showing reactivity in the Gn and Gc-specific ELISAs, with Gn-specific antibodies showing comparatively stronger early-onset reactivity (FIGS. 7a and b). A second vaccine dose at day 21 pv, significantly (P<0.05) increased specific reactivity with both antigens at day 28 pv (FIG. 7). Serum reactivity index (SRI), a metric for vaccine-induced antibody response in vaccinated animals, showed an increase in OD values ranging from 4 to 9.6 fold, to the Gn antigen (FIG. 7c) and 8 to 22.4 fold to the Gc antigen (FIG. 7d). For both antigens, peak induction of antibody response was observed at day 28 pv (FIGS. 7a and b).

Figure 8:
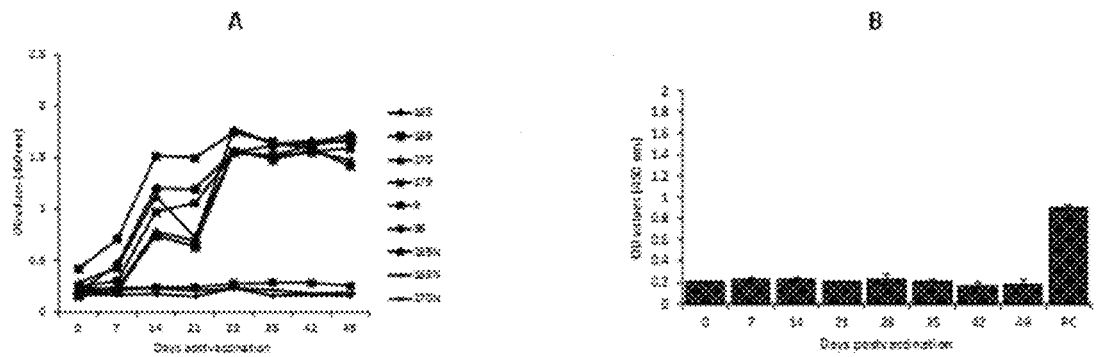
FIG. 8 shows indirect IgG ELISA demonstrating RVFV anti-Gn and anti-N antibody response in the vaccinated sheep. A) Reactivity of sera with Gn antigen indicates a time-dependent increase in antibody response, whereas in N-ELISA, reactivity remains at baseline prevaccination levels at all time points for all sera obtained from three sheep tested, #169N, 163N and 170N. B) Comparison of the reactivity of sera obtained from sheep vaccinated with the glycoprotein-based subunit vaccine to sera obtained from RVFV MP12 infected sheep, the positive control serum (PC). The N antigen was positively reactive with only the positive control serum indicated by high mean OD value; day 0 to day 49 sera were obtained from sheep #169. The cut-off value for individual sheep in Gn-ELISA: #163=0.354; #169=0.167; #170=0.507; #179=0.365; #36=0.252; #9=0.668. The cut-off value in N-ELISA for individual sheep tested: #169N=0.288; #163N=0.237; #170N=0.212. A cut-off value was determined for each sheep as described in materials and methods.

Example 6. DIVA Compatibility of Recombinant RVFV GnGc Glycoprotein Subunit Vaccine A DIVA concept analysis by indirect ELISA was carried out using the Gn protein, as a positive diagnostic antigen, and N protein, as a negative marker, to detect specific antibodies in vaccinated sheep. To exclude excessive background in the ELISA due to reactivity with co-purified baculovirus and/or insect cell proteins, an E. coli-expressed N protein was sued as a negative marker antigen. Using sera from vaccinated sheep, an increase in immunoreactivity with Gn antigen was observed from day 7 pv to day 28 pv, which later plateaued until the end of the experiment (FIG. 8a). In contrast, immunoreactivity with N-antigen was barely detectable, remaining at baseline levels throughout the experiment (FIG. 8a). To confirm the specific immunoreactivity of the E. coli-expressed N protein as a suitable marker antigen in ELISA, a day-28 MP12 postinfection antiserum (positive control) was tested in ELISA alongside sera obtained from sheep #169, vaccinated with the glycoprotein-based vaccine (FIG. 8b). Reactivity with these sera remained at baseline negative levels at all the time-points, whereas the MP12 control serum showed strong reactivity as indicated by a high OD value (P<0.05).

Figure 9:
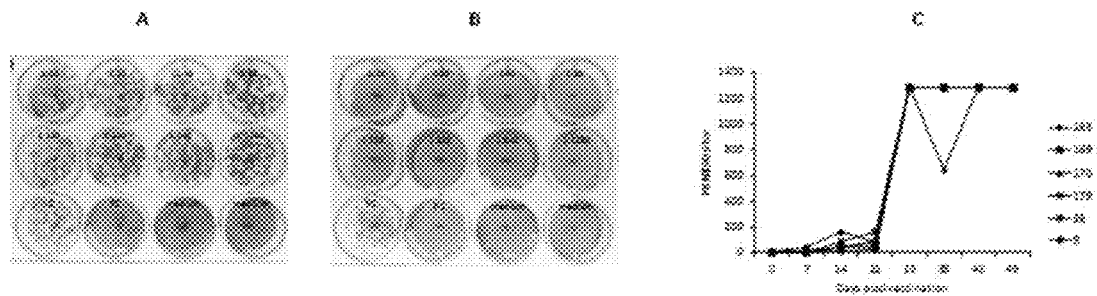
FIG. 9 shows a plaque reduction neutralization test (PRNT80) demonstrating a negative (A) and a positive (B) result. Protective levels of neutralizing antibody titers (≥1:40) are detectable in the animals within 2 weeks postvaccination. A marked increase in neutralizing antibody response is detected in all animals following administration of the second vaccine dose (C).

Example 7. Recombinant RVFV Glycoproteins Elicit Strong Neutralizing Antibody Response To assess the vaccine-induced neutralizing antibody response, a plaque reduction neutralization assay was performed (FIG. 9). An attenuated RVFV virus strain, MP12, was used. A serum neutralizing antibody titer of 1:40 is considered a protective response. Five of the six vaccinated sheep showed protective neutralizing titers at day 14 pv in response to the primary vaccination with antibody titers ranging from 1:40 to 1:160; one sheep, #9, showed protective neutralizing titer of 1:40 as early as day 7 pv (Table 3).

For this example, a total of 3 animals was assigned randomly to each of the 4 groups (total 12 animals). Following one week of acclimatization, animals were immunized subcutaneously with 50 ug each of Gc/Gn protein (total 100 μg) emulsified in either ISA25, ISA206, ISA206 plus InAcT (inulin acetate) or ISA206+InAcT-hisTAG adju-

TABLE 3

Reciprocal $PRNT_{80}$ titers in sheep in response to vaccination with RVFV recombinant GnGc glycoprotein subunit vaccine.

| Sheep ID No. | Reciprocal $PRNT_{80}$ titers | | | | | | | |
|---|---|---|---|---|---|---|---|---|
| | Day 0 prevac | Day 7 pv | Day 14 pv | Day 21 pv | Day 28 pv | Day 35 pv | Day 42 pv | Day 49 pv |
| 169 | 0 | 0 | 40 | 40 | 1280> | 1280> | 1280> | 1280 |
| 163 | 0 | 0 | 10 | 20 | 1280> | 640 | 1280> | 1280 |
| 170 | 0 | 0 | 40 | 80 | 1280> | 1280> | 1280> | 1280> |
| 179 | 0 | 0 | 40 | 80 | 1280> | 1280> | 1280> | 1280 |
| 9 | 0 | 40 | 160 | 80 | 1280> | 1280> | 1280 | 1280 |
| 36 | 0 | 0 | 80 | 160 | 1280> | 1280 | 1280 | 1280 |
| Mean | 0 | nd | 62 | 77 | 1280> | nd | 1280> | 1280> |
| Range | 0 | nd | 10-160 | 20-160 | 1280> | 540-1280> | 1280-1280> | 1280-1280> | prevac = pre-vaccination; pv = post-vaccination; nd = not determinable.

Protective levels of virus neutralizing titers were maintained in all of the sheep until day 21 pv with three of the five sheep (#170, #179, #36) showing a titer increase. A second vaccine dose administered at day 21 pv significantly boosted response in all six sheep above 1:1,280 titer, a week later, at day 28 pv (Table 3). Neutralizing antibody titers remained high in all sheep (with the exception of sheep #163, which showed a titer of 1:640 at day 35 pv) ranging from 1,280 to >1,280 until the end of the experiment (Table 3).

Figure 10:
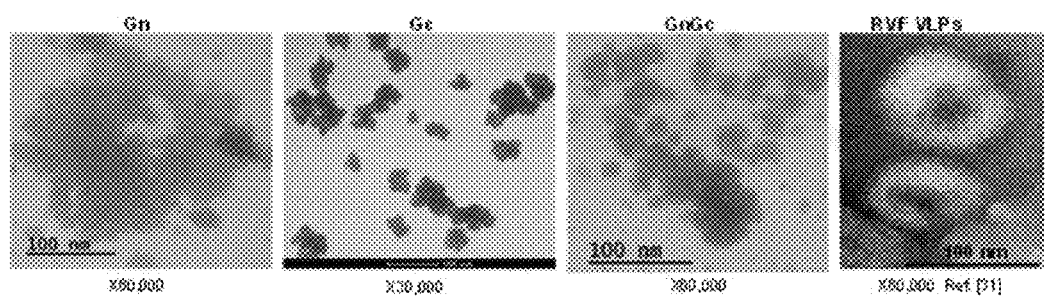
FIG. 10 shows an electronmicrograph of purified recombinant RVFV proteins used to vaccinate sheep. Gn, Gc and the reconstituted GnGc show as clumps of protein aggregates that are structurally distinct from RVF VLPs

Example 8. Electron Microscopy to confirm that the recombinant proteins, Gn and Gc, did not reassemble to form VLPs following mixing the recombinant proteins into vaccine formulation, the proteins were analyzed by transmission electron microscopy. Images showed clumps of protein aggregates that showed no resemblance to VLPs (FIG. 10).

Example 9. Adjuvant Combination Formulations

Immunization of sheep was carried out with a total of 1 ml vaccine, containing 50 ug of Gc and Gn recombinant protein emulsified with the adjuvants described in Table 4.

vant, prepared according to manufacturer's instructions. Total volume injected was 1 ml, divided into 2×0.5 ml doses.

Example 10. Characterization of Antibody Responses to Vaccination

Figure 11:
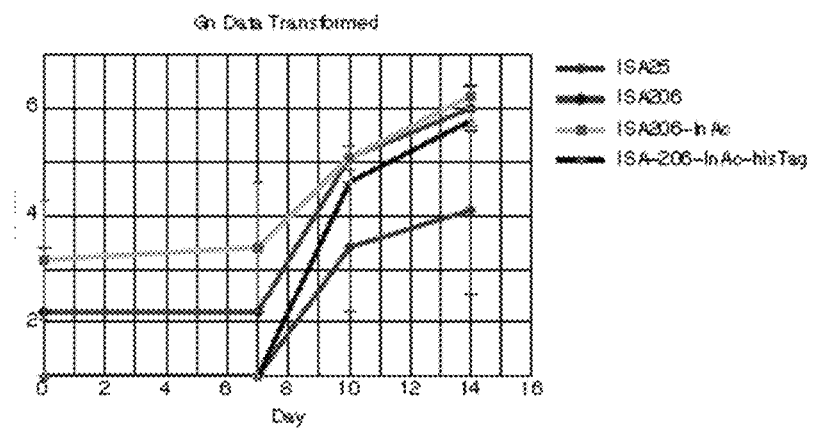
FIG. 11 shows analysis of vaccine-induced IgG host antibody response by antigen-specific indirect ELISAs for Gn using ISA25, ISA206, ISA206-InAc and ISA-206 InAc-hisTag adjuvants.
Figure 12:
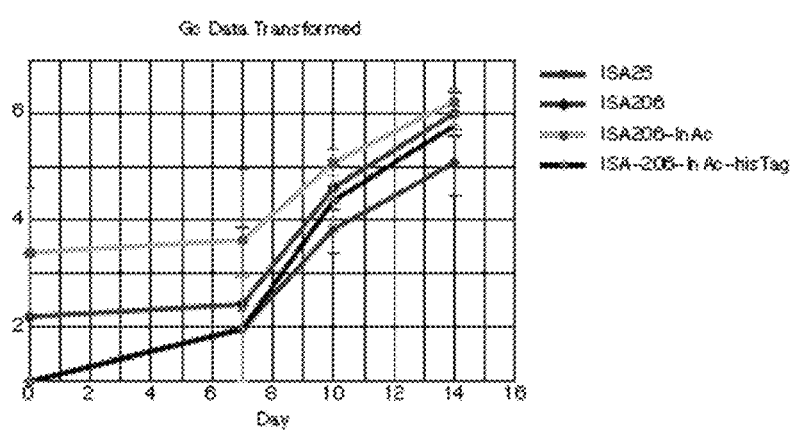
FIG. 12 shows analysis of vaccine-induced IgG host antibody response by antigen-specific indirect ELISAs for Gc using ISA25, ISA206, ISA206-InAc and ISA-206 InAc-hisTag adjuvants.

Blood samples were collected weekly in vacutainer Serum Preparation Tubes (total 30 ml) beginning 1 week prior to immunization, and continuing through 3 weeks post-vaccination. Antibody titres were determined by direct ELISA at Medgene Labs, and archived samples provided to KSU for Virus Neutralization Assay. Briefly, whole recombinant antigen (Gc, Gn) was used to coat Immunolon ELISA plates overnight. Plates were blocked, and then serial dilutions of serum applied in triplicate to each well. Detection of serum binding was by isotype-specific secondary antisera, conjugated to HRP and commercial TMB substrate (Pierce Biotechnology). A primary goal was to determine the rate of onset, maximal serum titre, and rate of decay of immunity. Results of the assay may be seen in FIGS. 11 and 12. As demonstrated in the figures, ISA206 provided the best overall induction, including that the addition of InAcT also resulted in increased response compared to ISA25. In order

TABLE 4

Adjuvant formulations.

| Adjuvant | Source | Characteristics | Approval Status |
|---|---|---|---|
| ISA25 | Seppic | Water-in-oil, used in preliminary studies | In commercial use, CVB approved. |
| ISA206 | Seppic | Water-in-oil, similar to Freund's Incomplete | Strong immunity, similar to ISA25 but expected 10-100 fold greater response. |
| ISA206 + InAcT | Seppic/Medgene | Water-in-oil, plus TLR4 agonist | Expected boost in Immunity to ISA206. |
| ISA206 + InAcT-hisTAG | Seppic/Medgene | Water-in-oil, plus TLR4 agonist, plus opsonization inducer. | Expected boost in Immunity to ISA206. | of effectiveness: ISA206+InAcT>ISA206>ISA206+InAcT+HisTag antibody>ISA25.

Example 11. Characterization of T Cell Responses to Vaccination

A total of 50 ml of blood will be collected from each animal in EDTA on days 0, 4, 7, 14, and 21, cells purified by gradient sedimentation, and placed in culture with the target antigens. T cell proliferation will be assessed 3 days post-culture using a colorimetric BrdU based ELISA (Roche Life Sciences). Standardized proliferation will be assessed using prepared T cell lines, in order to define the specificity of T cell reactivity to each antigen. In addition, the proportion of T cell subsets and generation of specific cytokine profiles will be assessed by flow cytometry using a panel of sheep-specific monoclonal antibodies available in our laboratory.

Example 12. Confirmation of Protective Responses In Vitro

In order to confirm the protection afforded by the immune response generated by each adjuvant, serum samples harvested from the test animals will be sent to collaborators at Kansas State University for testing in serum neutralization assays using MP12 or wild-type RVFV. This will confirm that the immunoreactivity observed with each adjuvant formulation is reflected in apparent protection from virus infection.

Compliance Requirements

All experiments may be carried out in BSL2, and existing facilities and infrastructure are available. Currently approved SDSU Animal Protocols cover the experiments described (Protocol number 12-037A).

It will be understood that particular embodiments described herein are shown by way of illustration and not as limitations of the disclosure. The principal features of this disclosure can be employed in various embodiments without departing from the scope of the disclosure. Those skilled in the art will recognize, or be able to ascertain using no more than routine study, numerous equivalents to the specific procedures described herein. Such equivalents are considered to be within the scope of this disclosure and are covered by the claims. All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

We claim herein:

1. An isolated protein comprising a fusion protein containing an amino acid sequence as set forth in SEQ ID NO:4, wherein the carboxyl terminus of said SEQ ID NO:4 is operatively linked to a protease cleavage site having six carboxyl-terminal histidine residues.

2. The isolated protein of claim 1, wherein said protein consists of an amino acid sequence as set forth in SEQ ID NO:4 operatively linked at the carboxyl terminal alanine to a protease cleavage site having six carboxyl-terminal histidine residues, and wherein said protein induces neutralizing antibodies against Rift Valley Fever Virus in a subject at primary dose.

3. The isolated protein of claim 1, wherein the protease cleavage site is the TENT protease site of a pFastBac/CT TOPO vector.

* * * * *